United States Patent
Gwag et al.

(10) Patent No.: US 11,826,329 B2
(45) Date of Patent: Nov. 28, 2023

(54) COMPOSITIONS AND METHODS FOR TREATING REPERFUSION INJURY OR HEMORRHAGE AFTER RECANALIZATION THERAPY

(71) Applicant: GNT Pharma Co., Ltd., Yongin-si (KR)

(72) Inventors: Byoung Joo Gwag, Yongin-Si (KR); Chun San An, Suwon-Si (KR); Jing Yu Jin, Suwon-Si (KR); Sung Ig Cho, Seoul (KR); Fangmeng Zhu, Hangzhou Zhejiang (CN); Xinliang Xu, Dongyang Zhejiang (CN); Weiqiang Zhan, Alpharetta, GA (US); Fuxin Liu, Hangzhou Zhejiang (CN); Soon-Mi Won, Hwaseong-Si (KR)

(73) Assignee: GNT Pharma Co., Ltd., Gyeonggi-do (KR)

( * ) Notice: Subject to any disclaimer, the term of this patent is extended or adjusted under 35 U.S.C. 154(b) by 0 days.

(21) Appl. No.: 17/197,736

(22) Filed: Mar. 10, 2021

(65) Prior Publication Data
US 2021/0283080 A1 Sep. 16, 2021

Related U.S. Application Data

(60) Provisional application No. 62/988,187, filed on Mar. 11, 2020.

(51) Int. Cl.
| | |
|---|---|
| *A61K 31/196* | (2006.01) |
| *A61K 45/06* | (2006.01) |
| *A61P 7/02* | (2006.01) |
| *A61K 38/48* | (2006.01) |
| *A61P 9/10* | (2006.01) |

(52) U.S. Cl.
CPC .......... *A61K 31/196* (2013.01); *A61K 38/482* (2013.01); *A61K 45/06* (2013.01); *A61P 7/02* (2018.01); *A61P 9/10* (2018.01)

(58) Field of Classification Search
CPC ................. A61K 31/196; A61P 7/02
See application file for complete search history.

(56) References Cited

FOREIGN PATENT DOCUMENTS

| | | |
|---|---|---|
| CN | 102617383 A | 8/2012 |
| KR | 2009/0113424 A | 11/2009 |
| WO | WO-2004/000786 A1 | 12/2003 |
| WO | WO-2006/126825 A1 | 11/2006 |
| WO | WO-2021/181159 A1 | 9/2021 |

OTHER PUBLICATIONS

Gwag et al., "Marked Prevention of Ischemic Brain Injury by Neu2000, an NMDA Antagonist and Antioxidant Derived from Aspirin and Sulfasalazine," Journal of Cerebral Blood Flow & Metabolism, 27: 1142-1151 (2007).
International Search Report and Written Opinion for International Application No. PCT/IB2021/000136 dated Aug. 3, 2021.

*Primary Examiner* — Kevin E Weddington
(74) *Attorney, Agent, or Firm* — Foley Hoag LLP; David P. Halstead

(57) ABSTRACT

The present invention relates to pharmaceutical compositions and methods for treating ischemic stroke in humans, using a tetrafluorobenzyl derivative of formula (I) or a pharmaceutically acceptable salt thereof conjointly with a thrombolytic drug, endovascular thrombectomy, or both (e.g., endovascular thrombectomy and a thrombolytic drug). Administration of a tetrafluorobenzyl derivative of formula (I) or its pharmaceutically acceptable salt can reduce reperfusion injury and other adverse events in patients conjointly receiving a thrombolytic drug, endovascular thrombectomy, or endovascular thrombectomy with a thrombolytic drug.

19 Claims, 9 Drawing Sheets

COMPOSITIONS AND METHODS FOR TREATING REPERFUSION INJURY OR HEMORRHAGE AFTER RECANALIZATION THERAPY

RELATED APPLICATION

This application claims a right of priority to and/or the benefit of the filing date of U.S. Provisional Application No. 62/988,187, filed on Mar. 11, 2020, which is hereby incorporated by reference in its entirety.

FIELD OF THE DISCLOSURE

The present invention relates to pharmaceutical compositions comprising a tetrafluorobenzyl compound of formula (I) or its pharmaceutically acceptable salt thereof and methods for treating patients with ischemic stroke, coronary artery thrombosis, venous thromboembolism, acute myocardial infarction, occluded catheters, pediatric pleural effusions, and prosthetic valve thrombosis, who may be concomitantly treated with recanalization therapy using a thrombolytic drug, endovascular thrombectomy, or endovascular thrombectomy with a thrombolytic drug.

BACKGROUND

Stroke is a leading cause of death and long-term disability worldwide. Stroke is a disease in which a blood vessel to the brain is either blocked by a clot or bursts. Interruption of blood supply to the brain by local thrombosis, embolic particles, or blood vessel rupture can cause primary neuronal death in the ischemic core, accompanied by secondary death in the ischemic penumbra as a result of activation of multiple death pathways. Therapeutically, thrombolytic and anticoagulant drugs are used to counteract these events by increasing reperfusion and modifying coagulation. Over the last decades, the number of people suffering or dying from stroke has increased worldwide, suggesting the continuously increasing global burden of stroke (Feigin et al, 2016).

Only intravenous thrombolysis with recombinant tissue plasminogen activator (rt-PA) was approved for the effective treatment of acute ischemic stroke patients within 4.5 hours of symptomatic onset until 2015 [Benjamin et al, 2018; The National Institute of Neurological Disorders and Stroke rt-PA Stroke Study Group, 1995]. Clinical benefits were observed when intravenous rt-PA was administered to ischemic stroke patients within 6 hours of symptomatic onset (Fugate and Rabinstein, 2014). While intravenous administration of rt-PA significantly improved the rate of survival and reduced disability, it increased intracranial hemorrhagic complication approximately by 6.4% and showed 4-32% of cerebral arterial recanalization depending upon size and types of the occluded vessel [Benjamin et al, 2018; The ATLANTIS, ECASS, and NINDS rt-PA Study Group Investigators, 2004]. Other intravenous thrombolytic drugs including urokinase have been prescribed to treat acute ischemic stroke patients (Dong et al, 2017).

Several clinical trials have demonstrated benefit and safety of endovascular therapy (EVT) for acute ischemic stroke patients involving mechanically removing a clot in the anterior circulation since 2015 (SWIFT PRIME, REVASCAT, MR CLEAN, EXTEND-IA, ESCAPE). The mechanical thrombectomy carried out within 6 hours after the onset of symptom significantly improved functional outcome for acute ischemic stroke patients with proximal anterior circulation occlusion. The beneficial effects were verified for acute ischemic stroke patients with a large vessel occlusion in the anterior circulation who received endovascular thrombectomy within 6 to 24 hours after the stroke onset in DAWN trial (Nogueira et al, 2018). The 2018 American Heart Association (AHA)/American Stroke Association (ASA) Guidelines for the early management of patients with acute ischemic stroke recommended EVT, alone or with rt-PA thrombolytics, as a standard therapy for acute ischemic stroke patients with large vessel occlusion in the anterior circulation within 24 hours of the stroke onset [Powers et al., 2018].

While EVT, alone or with rt-PA thrombolytics, shows significant benefits to some acute ischemic stroke patients, such recanalization therapy can be accompanied by several complications including vessel and nerve injury, access-site hematoma, intracerebral and subarachnoid hemorrhage, extra-cranial hemorrhage, and pseudoaneurysm (Balami et al., 2018). Moreover, less than 50% of acute ischemic stroke patients subject to mechanical thrombectomy showed improved clinical outcomes, suggesting additional therapeutic need for better treatment of acute ischemic stroke patients (Chamorro, 2018).

Recanalization therapy produces beneficial effects for acute ischemic stroke patients but is accompanied by disastrous pathological process such as brain cell death primarily through excess activation of ionotropic glutamate receptors sensitive to N-methyl-D-aspartate (NMDA), excess production and accumulation of toxic free radicals, and apoptosis (Won et al, 2002). In fact, timely administration of NMDA antagonists and antioxidants significantly prevented brain injury and functional deficits in various animal models of stroke. However, over the past decades, nearly 200 clinical trials of neuroprotectants including NMDA receptor antagonists and antioxidants had failed in showing beneficial effects for acute ischemic stroke patients (Chamorro et al, 2016; Minnerup et al, 2012; Sutherland et al, 2012). This implies that efficacy of neuroprotectants verified in preclinical animal models of stroke is not translated to human stroke patients. Such translational failure of neuroprotectants from preclinical studies to clinical trials for stroke patients are attributable to (1) difference between animal models and human stroke patients, (2) poor quality of preclinical studies, and (3) serious adverse events of NMDA antagonists such as neurotoxicity in rats and psychosis in human (Farber et al., 2002; Bang, 2017).

SUMMARY

In some aspects, compositions having the compound of formula (I) are disclosed for treating an ischemic stroke patient receiving a thrombolytic therapy or receiving endovascular thrombectomy, or for reducing adverse events of a thrombolytic therapy, or for reducing reperfusion injury to the myocardium after coronary artery thrombectomy, or for reducing neurological deficits, reducing hemorrhagic transformation, and/or improving daily activity of living in ischemic stroke patients receiving a recanalization therapy with a thrombolytic drug, endovascular thrombectomy, or endovascular thrombectomy with a thrombolytic drug. Formula (I) is as follows:

[Chemical Formula 1]

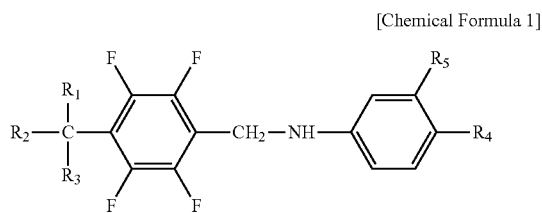

In this formula, for these aspects, $R_1$, $R_2$, and $R_3$, are, independently, hydrogen or halogen; $R_4$ is hydroxy, alkyl, alkoxy, halogen, alkanoyloxy, or nitro; and $R_5$ is carboxylic acid, carboxylic acid ester, carboxyamide, sulfonic acid, halogen, or nitro, or a pharmaceutically acceptable salt thereof.

In some embodiments, the compound of formula (I) is selected from the following: 2-Hydroxy-5-(2,3,5,6-tetrafluoro-4-trifluoromethylbenzylamino)benzoic acid, (hereinafter, referred to as '2-Hydroxy-TTBA' or "nelonemdaz"); 2-Nitro-5-(2,3,5,6-tetrafluoro-4-trifluoromethylbenzylamino)benzoic acid; 2-Chloro-5-(2,3,5,6-tetrafluoro-4-trifluoromethylbenzylamino)benzoic acid; 2-Bromo-5-(2,3,5,6-tetrafluoro-4-trifluoromethylbenzylamino)benzoic acid; 2-Methyl-5-(2,3,5,6-tetrafluoro-4-trifluoromethylbenzylamino)benzoic acid; 2-Methoxy-5-(2,3,5,6-tetrafluoro-4-trifluoromethylbenzylamino)benzoic acid; 5-(2,3,5,6-tetrafluoro-4-trifluoromethylbenzylamino)-2-trifluoromethoxybenzoic acid; 2-Nitro-4-(2,3,5,6-tetrafluoro-4-trifluoromethylbenzylamino)phenol; 2-Chloro-4-(2,3,5,6-tetrafluoro-4-trifluoromethylbenzylamino)phenol; 2-Hydroxy-5-(2,3,5,6-tetrafluoro-4-trifluoromethylbenzylamino)benzamide; 2-Hydroxy-5-(2,3,5,6-tetrafluoro-4-trifluoromethylbenzylamino)benzene sulfonic acid; Methyl 2-hydroxy-5-(2,3,5,6-tetrafluoro-4-trifluoromethylbenzylamino)benzoate; 2-Ethanoyloxy-5-(2,3,5,6-tetrafluoro-4-trifluoromethylbenzylamino)benzoic acid; 2-Propanoyloxy-5-(2,3,5,6-tetrafluoro-4-trifluoromethylbenzylamino)benzoic acid; and 2-Cyclohexanecarbonyloxy-5-(2,3,5,6-tetrafluoro-4-trifluoromethylbenzylamino)benzoic acid; or a pharmaceutically acceptable salt thereof. In some embodiments, the composition has 50 mg to 2000 mg of the compound of formula (I) or a pharmaceutically acceptable salt thereof.

In some aspects, a vial having any of these disclosed compositions has 50 mg to 2000 mg of the compound of formula (I) or a pharmaceutically acceptable salt thereof dissolved in water for injection at pH 8-11. In some aspects, a vial having any of these disclosed compositions has tris(hydroxymethyl)aminomethane [THAM]-buffered and sterile-filtered 50 mg to 2000 mg of the compound of formula (I) or a pharmaceutically acceptable salt thereof filled with $N_2$ gas overhead, wherein the vial is reconstituted by sterile water for injection. In some aspects, a vial having any of these disclosed compositions has sterile 50 mg to 2000 mg of the compound of formula (I) or a pharmaceutically acceptable salt thereof filled with and $N_2$-gas overhead, wherein the vial is reconstituted by THAM buffer.

In some aspects, methods of treating an ischemic stroke patient receiving a thrombolytic therapy include administering to the patient the compound or composition of any of the other disclosed aspects. In some aspects, methods of treating an ischemic stroke patient receiving endovascular thrombectomy, optionally conjointly with a thrombolytic therapy, include administering to the patient the compound or composition of any of the other disclosed aspects. In some aspects, methods of reducing adverse events of a thrombolytic therapy such as rt-PA, modified rt-PA, or urokinase in a patient with venous thromboembolism, myocardial infarction, catheter occlusion, pediatric pleural effusion, catheter-directed therapy, and/or prosthetic valve thrombosis, include administering to the patient the compound or composition of any of the other disclosed aspects. In some aspects, methods of reducing reperfusion injury to the myocardium after coronary artery thrombectomy in a patient, include administering to the patient a compound or composition of any of the other disclosed aspects.

In some aspects, methods of reducing neurological deficits and/or improving daily activity of living in an ischemic stroke patient receiving a recanalization therapy with a thrombolytic drug, endovascular thrombectomy, or endovascular thrombectomy with a thrombolytic drug, include administrating to the patient a compound of formula (I) of any of the other disclosed aspects or a pharmaceutically acceptable salt thereof. In some aspects, methods of reducing hemorrhagic transformation in an ischemic stroke patient conjointly receiving a recanalization therapy with a thrombolytic drug, endovascular thrombectomy, or endovascular thrombectomy with a thrombolytic therapy, include administrating to the patient a compound of formula (I) or a pharmaceutically acceptable salt thereof of any of the other disclosed aspects. In some aspects, methods of reducing adverse events of a thrombolytic therapy in a patient with venous thromboembolism, myocardial infarction, catheter occlusion, pediatric pleural effusions, catheter-directed therapy, and/or prosthetic valve thrombosis, include administrating to the patient a compound of formula (I) or a pharmaceutically acceptable salt thereof of any of the other disclosed aspects. In some aspects, methods of reducing reperfusion injury to the myocardium after coronary artery thrombectomy in a patient, include administrating to the patient a compound of formula (I) or a pharmaceutically acceptable salt thereof of any of the other disclosed aspects.

In some embodiments, the compound of formula (I) is 2-Hydroxy-5-(2,3,5,6-tetrafluoro-4-methylbenzylamino) benzoic acid ("nelonemdaz") or its potassium salt ('nelonemdazK'). In some embodiments, the compound is nelonemdazK and is administered in a dose from 250 mg to 1500 mg twice daily for 1-5 days. In some embodiments, nelonemdazK is administered to ischemic stroke patients receiving recanalization therapy at a total dose of 6,000 mg for 5 days (1st 1500 mg+2nd~10th 500 mg each around at 12 h intervals; all IV infusion over 30 min) or a total dose of 5,250 mg (1st 750 mg+2nd~10th 500 mg around at 12 h dose for 5 days). In some embodiments, the compound is administered in a composition as defined in any of the disclosed aspects. In some embodiments, the patient is a human.

In some aspects, methods of improving recanalization therapy in a subject include administering to the subject a therapy that comprises both NR2B antagonism and antioxidant properties. In some aspects, methods of improving recanalization therapy in a subject include administering to the subject concurrently both a therapy that comprises NR2B antagonism and a second therapy that comprises antioxidant properties.

In some embodiments, recanalization therapy comprises thrombolytic drug, endovascular thrombectomy, or both. In some embodiments, subject is an ischemic stroke patient. In some embodiments, improving recanalization therapy comprises reduction of reperfusion injury or other adverse events in the subject. In some embodiments, NR2B antagonism is a safe (fast/weak) antagonism. In some embodiments, therapy comprises an agent that has both of said NR2B antagonism and antioxidant properties (e.g., nelonemdaz or nelonemdazK). In some embodiments, therapy comprises a first agent that has NR2B antagonism property and a second agent that has antioxidant property. In some embodiments, first agent and second agent are administered conjointly.

BRIEF DESCRIPTION OF THE DRAWINGS

The above and other objects, features and other advantages of the present invention will be more clearly understood from the following detailed description taken in conjunction with the accompanying drawings, in which:

FIG. 2A shows that administration of nelonemdazK increases ratio of mRS 0-2 (functional independence) and 0 (no symptoms at all) in acute ischemic stroke patients.

FIG. 2B shows that administration of nelonemdazK results in better functional recovery for moderate to severe (NIHSS score≥6) ischemic stroke patients compared to patients including mild (4≤NIHSS score≤5) stroke. Both FIG. 2A and FIG. 2B relate to the beneficial effects of nelonemdaz in acute ischemic stroke patients treated with a thrombolytic drug ("ENIS" trial). The bars, from left to right are for placebo, nelonemdazK, placebo, nelonemdazK.

FIG. 3A shows that administration of low or high dose nelonemdazK increases ratio of mRS 0-2 (functional independence) and 0 (no symptoms at all) in acute ischemic stroke patients treated with endovascular thrombectomy.

FIG. 3B shows that administration of low or high dose nelonemdazK significantly increases ratio of mRS 0 in acute ischemic stroke patients treated with endovascular thrombectomy at 1, 4, and 12 weeks after drug treatment. The vertical bars for each time triplet, from left to right, are placebo, nelonemdazK(low), and nelonemdazK(high).

FIG. 3C shows that administration of low or high dose nelonemdazK increases ratio of Barthel Index score higher than 90 (good recovery of daily living activities) in acute ischemic stroke patients treated with endovascular thrombectomy at 12 weeks after drug treatment. FIG. 3A, FIG. 3B, and FIG. 3C relate to the beneficial effects of nelonemdaz in acute ischemic stroke patients treated with endovascular thrombectomy ("SONIC" trial).

DETAILED DESCRIPTION

Figure 1A:
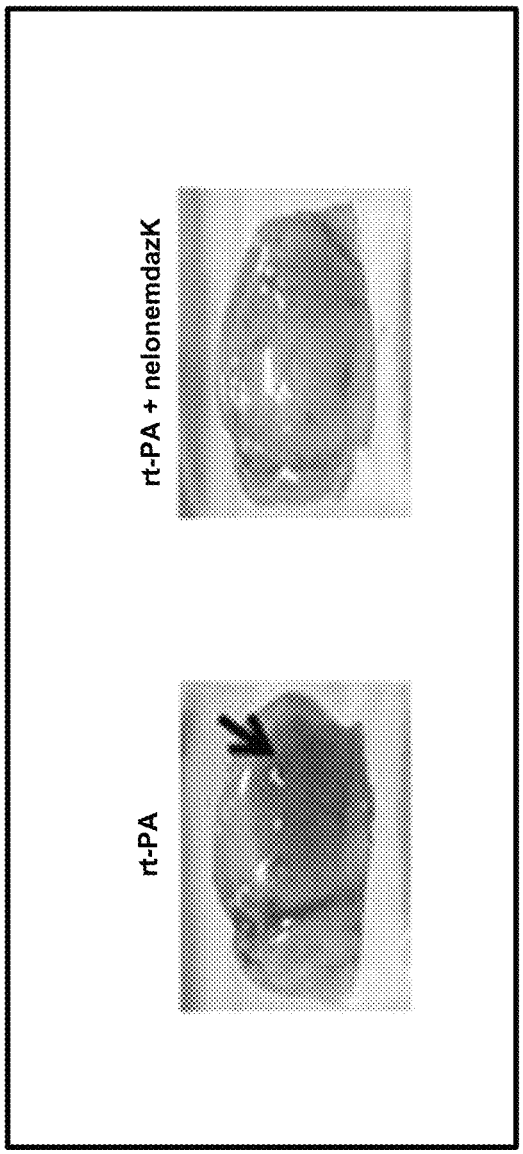
FIG. 1A: Prevention of rt-PA-induced hemorrhagic transformation following 3-h occlusion of middle cerebral artery in adult rats. Upper and lower panels show that nelonemdazK [2-Hydroxy-5-(2,3,5,6-tetrafluoro-4-trifluoromethylbenzylamino)benzoic acid potassium salt] prevents hemorrhagic transformation in the brain of adult rats treated with rt-PA after 3-h occlusion of middle cerebral artery.

The present disclosure is directed to compositions and methods relating to one or more tetrafluorobenzyl compounds of formula (I), their pharmaceutically acceptable salts and drug product formulations thereof for the treatment of ischemic patients receiving a recanalization therapy with a thrombolytic drug (such as rt-PA, modified rt-PA, urokinase, or other suitable thrombolytic drug), EVT, or EVT with a thrombolytic drug.

The present disclosure is directed, at least in part, to compositions and methods relating to one or more tetrafluorobenzyl compounds of formula (I), and pharmaceutically acceptable salts and drug product formulations thereof for the treatment for reducing hemorrhagic transformation induced by administration of thrombolytic drugs.

In some embodiments, the present disclosure is directed to a process for producing a drug product formulation comprising 2-Hydroxy-5-(2,3,5,6-tetrafluoro-4-trifluoromethylbenzylamino)benzoic acid potassium salt.

Accordingly, the present disclosure provides pharmaceutical compositions and methods relating to a tetrafluorobenzyl compound of formula (I), or a pharmaceutically acceptable salt thereof useful for the treatment of ischemic stroke patients receiving a recanalization therapy with a thrombolytic drug, EVT, or EVT with a thrombolytic drug.

The present disclosure provides pharmaceutical compositions and methods relating to a tetrafluorobenzyl compound of formula (I), or a pharmaceutically acceptable salt thereof useful for reducing hemorrhagic transformation induced by administration of thrombolytic drugs.

The present disclosure provides a process for producing a drug product formulation containing 2-Hydroxy-5-(2,3,5,6-tetrafluoro-4-trifluoromethylbenzylamino)benzoic acid potassium salt.

The present disclosure provides a compound of formula (I) or a pharmaceutically acceptable salt thereof for treating ischemic stroke patients receiving a recanalization therapy with a thrombolytic drug, EVT, or EVT with a thrombolytic drug:

[Chemical Formula 1]

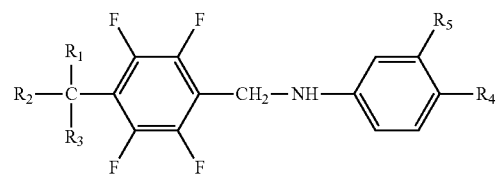

wherein $R_1$, $R_2$, and $R_3$ are each independently hydrogen or halogen, preferably each H or each F;

R₄ is hydroxy, alkyl, alkoxy (e.g., unsubstituted or substituted with halogen), halogen, alkanoyloxy, or nitro; and R₅ is carboxylic acid, carboxylic acid ester (e.g., an alkyl ester), carboxamide, sulfonic acid, halogen, or nitro.

In certain embodiments, an alkyl group is a $C_1$-$C_6$ alkyl and more preferably $C_1$-$C_4$ alkyl, e.g., methyl, ethyl, propyl, isopropyl. n-butyl, sec-butyl, or tert-butyl.

In certain embodiments, an alkoxy group is a $C_1$-$C_6$ alkoxy and more preferably a $C_1$-$C_4$ alkoxy, e.g., methoxy, ethoxy, or propanoxy.

Halogen can be fluorine, chlorine, bromine, or iodine.

In certain embodiments, alkanoyloxy is $C_2$-$C_{10}$ alkanoyloxy and more preferably $C_3$-$C_8$ alkanoyloxy, e.g., ethanoyloxy (i.e., acetoxy), propanoyloxy, or cyclohexanecarbonyloxy.

In certain embodiments, a carboxylic acid ester can be a methyl, ethyl, isopropyl, or butyl ester.

The present disclosure provides methods relating to a tetrafluorobenzyl compound of formula (I), or a pharmaceutically acceptable salt thereof as defined herein for treating ischemic stroke patients receiving a recanalization therapy with a thrombolytic drug, EVT, or EVT with a thrombolytic drug.

The present disclosure provides methods relating to a tetrafluorobenzyl compound of formula (I), or a pharmaceutically acceptable salt thereof as defined herein for reducing hemorrhagic transformation induced by administration of thrombolytic drugs.

Preferred compounds of formula (I) include, but are not limited to:

2-Hydroxy-5-(2,3,5,6-tetrafluoro-4-trifluoromethylbenzylamino)benzoic acid, (hereinafter, referred to as '2-Hydroxy-TTBA', 'Neu2000' or 'nelonemdaz'),
2-Nitro-5-(2,3,5,6-tetrafluoro-4-trifluoromethylbenzylamino)benzoic acid,
2-Chloro-5-(2,3,5,6-tetrafluoro-4-trifluoromethylbenzylamino)benzoic acid,
2-Bromo-5-(2,3,5,6-tetrafluoro-4-trifluoromethylbenzylamino)benzoic acid,
2-Methyl-5-(2,3,5,6-tetrafluoro-4-trifluoromethylbenzylamino)benzoic acid,
2-Methoxy-5-(2,3,5,6-tetrafluoro-4-trifluoromethylbenzylamino)benzoic acid,
5-(2,3,5,6-tetrafluoro-4-trifluoromethylbenzylamino)-2-trifluoromethoxybenzoic acid.
2-Nitro-4-(2,3,5,6-tetrafluoro-4-trifluoromethylbenzylamino)phenol,
2-Chloro-4-(2,3,5,6-tetrafluoro-4-trifluoromethylbenzylamino)phenol (hereinafter, referred to as '2-Chloro-TTP'),
2-Hydroxy-5-(2,3,5,6-tetrafluoro-4-trifluoromethylbenzylamino)benzamide (hereinafter, referred to as '2-Hydroxy-TTA'),
2-Hydroxy-5-(2,3,5,6-tetrafluoro-4-trifluoromethylbenzylamino)benzene sulfonic acid (hereinafter, referred to as '2-Hydroxy-TTS'),
Methyl 2-hydroxy-5-(2,3,5,6-tetrafluoro-4-trifluoromethylbenzylamino)benzoate,
2-Ethanoyloxy-5-(2,3,5,6-tetrafluoro-4-trifluoromethylbenzylamino)benzoic acid (hereinafter, referred to as '2-Ethan-TTBA'),
2-Propanoyloxy-5-(2,3,5,6-tetrafluoro-4-trifluoromethylbenzylamino)benzoic acid (hereinafter, referred to as '2-Propan-TTBA'), or
2-Cyclohexanecarbonyloxy-5-(2,3,5,6-tetrafluoro-4-trifluoromethylbenzylamino)benzoic acid (hereinafter, referred to as '2-Cyclohexan-TTBA'),
or a pharmaceutically acceptable salt thereof.

In particularly preferred embodiments, the compound of formula (I) is 2-Hydroxy-5-(2,3,5,6-tetrafluoro-4-trifluoromethylbenzylamino)benzoic acid ('2-Hydroxy-TTBA'. 'Neu2000' or 'nelonemdaz') or a pharmaceutically acceptable salt thereof. In some embodiments, the compound of formula (I) has the structure

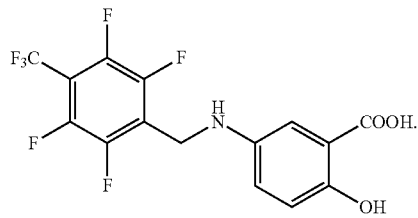 [SMILES: O=C(O)c1cc(NCc2c(F)c(F)c(C(F)(F)F)c(F)c2F)ccc1O]

The pharmaceutically acceptable salts of the compounds of the present invention include alkali metal salts, such as lithium, sodium or potassium salts, and alkaline earth metal salts, such as calcium or magnesium salts. Acid addition salts may be prepared by reacting the solution of pharmaceutically acceptable nontoxic salts such as hydrochloric acid, fumaric acid, maleic acid, succinic acid, acetic acid, citric acid, tartaric acid, carbonic acid, or phosphoric acid with the compound of the invention.

Tetrafluorobenzyl compounds of formula (I) and their pharmaceutically acceptable salts can be prepared by, for example, the reaction schemes presented in U.S. Pat. No. 7,511,074.

For example, a pharmaceutically acceptable salt of nelonemdaz can be prepared by the reaction scheme 1 below. However, the reaction scheme is offered for illustration and not intended to limit the scope of the disclosure. In the scheme, M is a pharmaceutically acceptable metal (such as lithium, sodium or potassium) or a conjugate acid of a basic organic compound such as diethylamine.

<Reaction Scheme 1>

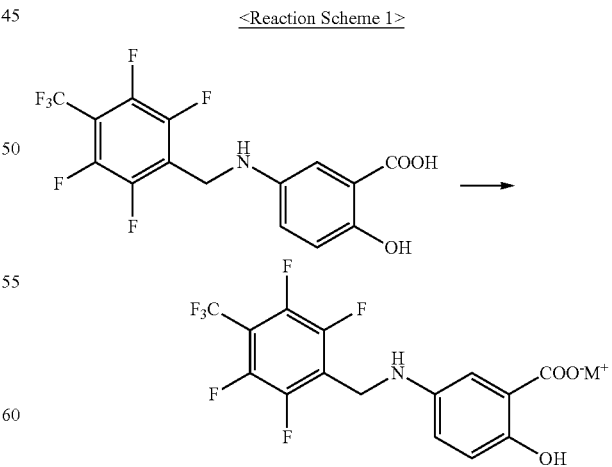

In some embodiments, a tetrafluorobenzyl compound of formula (I), or a pharmaceutically acceptable salt thereof, preferably 'nelonemdaz' ('2-Hydroxy-TTBA') or a pharmaceutically acceptable potassium salt thereof ("nelonemdazK'), is useful to reduce the neurological deficits and improved activity of daily living in ischemic stroke patients receiving a recanalization therapy by a thrombolytic drug such as rt-PA, EVT, or EVT with a thrombolytic drug.

In some embodiments, a tetrafluorobenzyl compound of formula (I), or a pharmaceutically acceptable salt thereof, preferably 'nelonemdaz' ('2-Hydroxy-TTBA') or a pharmaceutically acceptable potassium salt thereof ("nelonemdazK'), is useful to reduce the hemorrhagic transformation induced in ischemic stroke patients receiving a recanalization therapy by a thrombolytic drug such as rt-PA, EVT, or EVT with a thrombolytic drug.

The present disclosure also provides a composition comprising a tetrafluorobenzyl compound represented by the chemical formula (I) above or its pharmaceutically acceptable salt; and one or more pharmaceutically acceptable excipients or additives. The tetrafluorobenzyl compound represented by the chemical formula (I) above or its pharmaceutically acceptable salt may be administered alone. In some embodiments, the composition comprising a compound of formula (I) is administered with any convenient carrier, diluent, etc.

In some embodiments, the composition comprises from about 250 mg to about 2,000 mg of the compound of formula (I) per unit dosage form. In some embodiments, the composition is used to administer from about 250 mg to about 2,000 mg of the compound of formula (I) per dosing. In certain preferred embodiments, the composition comprises from about 100 mg to about 1,000 mg of the compound of formula (I) per unit dosage form. In certain preferred embodiments, the composition is used to administer from about 100 mg to about 1,000 mg of the compound of formula (I) per dosing. In particularly preferred embodiments, the composition comprises from about 50 mg to about 500 mg of the compound of formula (I) per dosing.

In some embodiments, a formulation for administration may be a single-dose unit or multiple-dose unit. In some embodiments, the composition comprises a single dose unit. In some embodiments, the composition comprises a multiple-dose unit.

The compounds and pharmaceutical compositions of the present disclosure may be administered in forms of, but not limited to, injectable formulation (for example, intramuscular, intraperitoneal, intravenous, infusion, subcutaneous, implant). The compositions of the present disclosure may be formulated in a suitable dosage unit comprising a pharmaceutically acceptable and non-toxic carrier, additive and/or vehicle, which all are generally used in the art, depending on the desired route of administration. Depot formulations capable of continuously releasing drug for an extended time are also within the scope of the present disclosure.

In some embodiments, the pharmaceutical compositions of the present disclosure may be administered conjointly with a thrombolytic drug, endovascular thrombectomy, or both (e.g., endovascular thrombectomy and a thrombolytic drug), or conjointly with a thrombolytic drug, endovascular thrombectomy, or endovascular thrombectomy with a thrombolytic drug. The terms "conjoint" and "conjointly" are as defined below.

As used herein the specification, "a" or "an" may mean one or more. As used herein in the claim(s), when used in conjunction with the word "comprising", the words "a" or "an" may mean one or more than one. As used herein "another" may mean at least a second or more.

The terms "administration" and or "administering" should be understood to mean providing a compound or a prodrug of a compound to a subject in need of treatment.

The phrase "pharmaceutically-acceptable carrier" as used herein means a pharmaceutically acceptable material, composition or vehicle, such as a liquid or solid filler, diluent, excipient, solvent, or encapsulating material. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose, sucrose, and mannitol; (2) starches, such as corn starch and potato starch; (3) cellulose, and its derivatives, such as hydroxypropyl methylcellulose, ethyl cellulose, cellulose acetate, and microcrystalline cellulose; (4) powdered tragacanth; (5) malt; (6) gelatin; (7) talc; (8) disintegrants, such as crosslinked polymers including crospovidone and croscarmellose sodium; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "subject" refers to a mammal, including, but not limited to, a human or non-human mammal, such as a bovine, equine, canine, ovine, or feline.

The term "substance" includes all ingredients that can be included in a pharmaceutical composition (e.g., water, other solvents, carriers, excipients).

The terms "conjoint" and "conjointly," in the context of administering compounds or compositions, indicate that two different compounds or compositions can be administered without separating their administration regimens from each other or without ceasing administration of one before starting the administration of the other one (e.g., they can be administered via an agent that includes both, they can otherwise be administered concurrently, they can be administered separately but without a significant time delay (e.g., 1 hour, 6 hours, 12 hours, 1 day, 2 days) between their administrations).

As used herein, the term "treating" or "treatment" includes reversing, reducing, or arresting the symptoms, clinical signs, and underlying pathology of a condition in a manner to improve or stabilize a subject's condition.

The term "therapeutic treatment" is art-recognized and includes administering to the subject a composition after the manifestation of an unwanted condition, such as ischemic stroke.

The compositions disclosed herein may comprise a pharmaceutically acceptable carrier. The pharmaceutical composition disclosed herein may be delivered by any suitable route of administration, including orally, buccally, sublingually, parenterally, and rectally, as by powders, ointments, drops, liquids, gels, tablets, capsules, pills, or creams. In certain embodiments, the pharmaceutical compositions are delivered generally (e.g., via oral administration). In certain other embodiments, the compositions disclosed herein are delivered rectally. In some embodiments, the compositions disclosed herein are delivered intravenously.

Actual dosage levels of the active ingredients in the pharmaceutical compositions may be varied to obtain an amount of the active ingredient that is effective to achieve the desired therapeutic response for a subject, composition, and mode of administration, without being toxic to the subject.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds employed in the pharmaceutical composition at levels lower than that required in order to achieve the desired therapeutic effect and gradually increase the dosage until the desired effect is achieved.

In some embodiments, the composition is provided in a sterile vial(s) comprising 50 mg to 2000 mg of the compound of formula (I) or its pharmaceutically acceptable salt dissolved in water (e.g., nanopure water) in the range of pH 8-11. Such compositions may be filtered and lyophilized, e.g., under a condition filled with nitrogen gas. The composition in the vial may then be reconstituted by sterile water for injection and further diluted into 0.9% normal saline before injection to human. Repeated lyophilization procedures can be carried out, e.g., until near white colored cakes are obtained, preferably free or substantially free of needle-shaped crystals.

In some embodiments, the composition is provided as a sterile vial(s) comprising 50 mg to 2000 mg of the compound of formula (I) or its pharmaceutically acceptable salt dissolved in tris(hydroxymethyl)aminomethane [THAM]-buffered water (e.g., nanopure water). Such compositions may be filtered and lyophilized, e.g., under $N_2$ gas-filled condition. The composition in the vial may then be reconstituted by sterile water for injection and further diluted into 0.9% normal saline before injection to human.

In some embodiments, the composition is provided as a sterile vial(s) comprising 50 mg to 2000 mg of the compound of formula (I) or its pharmaceutically acceptable salt dissolved in tris(hydroxymethyl)aminomethane [THAM]-buffered water. Such compositions may be filtered and lyophilized under $N_2$ gas-filled condition. The composition in the vial may then be reconstituted by THAM buffer for injection and further diluted into 0.9% normal saline before injection to human.

In some embodiments, encompassed are vials (e.g., sterilized vials) having a lyophilized form of the compound of formula (I) or a pharmaceutically acceptable salt thereof (e.g., in an amount from 50 mg to 2000 mg). In some embodiments, encompassed are post-reconstitution vials having a reconstituted form of the compound of formula (I) or a pharmaceutically acceptable salt thereof (e.g., in an amount from 50 mg to 2000 mg), for example as reconstituted by sterile water or THAM buffer, and optionally diluted into 0.9% normal saline.

The present disclosure also provides a use of the tetrafluorobenzyl compound represented by the chemical formula (I) above or its pharmaceutically acceptable salt for the treatment of ischemic stroke patients receiving a recanalization therapy with a thrombolytic drug, EVT, or EVT with a thrombolytic drug.

The present disclosure also provides a use of the tetrafluorobenzyl compound represented by the chemical formula (I) above or its pharmaceutically acceptable salt for reducing hemorrhagic transformation induced by administration of thrombolytic drugs.

The present disclosure also provides a use of the tetrafluorobenzyl compound represented by the chemical formula (I) above or its pharmaceutically acceptable salt for reducing thrombolytic drug (eg. rt-PA etc.)-induced adverse events in patients receiving a thrombolytic treatment due to thromboembolic disorders including venous thromboembolism (pulmonary embolism, deep vein thrombosis), ST-Elevation Myocardial Infarction (STEMI), IV catheter occlusion, catheter-directed therapy, prosthetic valve thrombosis, and coronary thrombectomy.

In some embodiments, the above chemical formula (I) or its pharmaceutically acceptable salt is administered to human in a dose from 100 mg to 4000 mg daily for 1-7 days the use mentioned above [0026]~[0028]. In certain preferred embodiments, nelonemdazK is administered to human in a dose from 250 mg to 3000 mg daily for 1-7 days. In some embodiments, nelonemdazK is administered by intravenous (IV) infusions to ischemic stroke patients receiving recanalization therapy for 5 days at following dosage schedule below:

(1) for a total dose of 6,000 mg nelonemdazK: 1500 mg for $1^{st}$ infusion, 500 mg for $2^{nd}$ infusion at 12±6 hr interval, and 500 mg each for $3^{rd}$-10th infusion
(2) for a total dose of 5,250 mg nelonemdazK: 750 mg for $1^{st}$ infusion, 500 mg for $2^{nd}$ infusion at 12±6 hr interval, and 500 mg each for $3^{rd}$-10th infusion
(3) for a total dose of 3,500 mg nelonemdazK: 750 mg for $1^{st}$ infusion, 250 mg for $2^{nd}$ infusion at 12±6 hr interval, and 250 mg each for $3^{rd}$-10th infusion
(4) For a total dose of 3,250 mg nelonemdazK: 500 mg for $1^{st}$ infusion, 250 mg for $2^{nd}$ infusion at 12±6 hr interval, and 250 mg each for $3^{rd}$-10th infusion However, the treatment methods (dose, treatment route, intervals, infusion type etc.) are not limited to the methods described above.

In various embodiments, the present invention relates to methods and pharmaceutical compositions of nelonemdaz and its derivatives for the treatment of patients with ischemic stroke patients and diseases receiving recanalization therapy. Moderate affinity and subtype-selective antagonists of NMDA receptors have been developed to investigate if they could reduce intolerable side effects of NMDA receptors (Cho et al., 2010). Memantine, a moderate NMDA receptor antagonist, was approved for the treatment of Alzheimer's disease, improved cognitive function in patients with mild to moderate vascular dementia without serious side effects (Orgogozo et al., 2002), and has shown beneficial effects in preclinical animal models of stroke (Seyedsaadat & Kallmes, 2019). NR2B-containing NMDA receptors are localized on extrasynaptic membranes as well as synapses and thus activated in excess by glutamate accumulated in the extracellular space following stroke attack, which can cause excitotoxic neuronal death. Several NR2B subunit selective antagonists have been developed as neuroprotective NMDA receptor antagonists (Wang & Shuaib, 2005). NR2B antagonists such as eliprodil and ifenprodil showed neuroprotective effects in preclinical models of stroke and no psychotomimetic effects in human (Muir & Lees, 2003). However, beneficial effects of such NR2B antagonists have not been reported against stroke patients.

While main antioxidants such as tirilazad, ebselen, and NXY-059 did not show beneficial effects in clinical trials for stroke patients, edaravone, a radical scavenger, was approved for the treatment of acute ischemic stroke patients within 24 h from the onset of symptoms in Japan in 2002. However, the therapeutic potential of edaravone is limited by serious adverse reactions including renal and hepatic disorders (Hishida, 2007).

Nelonemdaz is a single molecule with both NR2B-selective antagonist and antioxidant properties that has shown beneficial effects in preclinical animal models of stroke (Cho et al., 2010). We have conducted preclinical and clinical studies to examine the possibility that nelonemdaz may show safe profiles and beneficial effects in ischemic stroke patients treated with recanalization therapy. Administration of nelonemdaz did not produce neurotoxicity in rodents and psychosis in stroke patients as well as healthy human volunteers, reduced adverse events induced by rt-PA in rats, and significantly reduced disability without producing serious adverse events in two independent clinical trials for acute ischemic stroke patients treated with EV or a thrombolytic drug.

TABLES

TABLE 1a

Comparison of MK-801 and nelonemdazK for Olney lesion in adult rats

| Study Drug | | MK-801 | | | | | nelonemdazK | | | | | | |
|---|---|---|---|---|---|---|---|---|---|---|---|---|---|
| Dose (treatment route) | | 1 mg/kg (IP) | | 10 mg/kg (IP) | | | 200 mg/kg (IV) | | | | | | |
| Total number of rats | | 8 | | 8 | | | 20 | | | | 20 | | |
| Sex | | female | | male | | | female | | | | male | | |
| Number of rats per group | | 4 | 4 | 4 | 4 | 5 | 5 | 5 | 5 | 5 | 5 | 5 | 5 |
| Day of Sacrifice after drug treatment | | 1 | 3 | 1 | 3 | 1 | 3 | 5 | 9 | 1 | 3 | 5 | 9 |
| Number of | Retrosplenial cortex | 8 | | 8 | | | 0 | | | | 0 | | |
| rats | Hippocampus CA1 | 6 | | 7 | | | 0 | | | | 0 | | |
| showing | Dentate gyrus | 2 | | 1 | | | 0 | | | | 0 | | |
| neurotoxicity | Piriform cortex | 5 | | 3 | | | 0 | | | | 0 | | |
| in brain | Entorhinal cortex | 2 | | 3 | | | 0 | | | | 0 | | |
| areas of Olney lesion | Cortical amygdaloid nucleus | 1 | | 0 | | | 0 | | | | 0 | | |

Forty animals (20 rats for male, 20 rats for female) treated with vehicle did not show any neurotoxicity in brain.

TABLE 1b

Comparison of MK-801 and nelonemdazK for abnormal behavior in adult rats

| Study Drug | | MK-801 | | nelonemdazK | |
|---|---|---|---|---|---|
| Dose (treatment route) | | 1 mg/kg (IP) | 10 mg/kg (IP) | 200 mg/kg (IV) | |
| Total number of rats | | 8 | 8 | 40 (20 per each sex) | |
| Sex | | female | male | female | male |
| Number | Ataxia | 6 (75) | 3 (38) | 0 (0) | 0 (0) |
| (%) of | Decreased activity | 8 (100) | 4 (100) | 0 (0) | 0 (0) |
| rats | Repetitive jaw chewing | 4 (50) | 3 (38) | 0 (0) | 0 (0) |
| showing | Clenched paws | 7 (88) | 5 (50) | 0 (0) | 0 (0) |
| abnormal behavior | Abnormal body position lying on side | 2 (25) | 1 (13) | 0 (0) | 0 (0) |
| | Increased salivation | 2 (25) | 5 (50) | 0 (0) | 0 (0) |

Forty animals (20 rats for male, 20 rats for female) treated with vehicle did not show any abnormal behavior.

TABLE 2

Behavioral safety of nelonemdazK compared to aptiganel, an NMDA antagonist, in healthy volunteers

| | | nelonemdazK (Phase 1 in the USA) | | nelonemdazK (Phase 1 in China) | | aptiganel (Phase 1) |
|---|---|---|---|---|---|---|
| Type of adverse effects | | 95 healthy volunteers | | 70 healthy volunteers | | 94 healthy volunteers |
| | Side-effect | Drug (n = 73) | Placebo (n = 24) | Drug (n = 57) | Placebo (n = 14) | Drug-induced side effect |
| Number of | Hallucination | 0 | 0 | 0 | 0 | yes |
| subjects | Paranoia | 0 | 0 | 0 | 0 | yes |
| showing | Catatonia | 0 | 0 | 0 | 0 | yes |
| abnormal | Agitation | 0 | 0 | 0 | 0 | yes |
| behavior | Confusion | 0 | 0 | 0 | 0 | NA |

Phase 1 studies of aptiganel (Muir et al, 1994 & 1995); NA, data not available

TABLE 3

Behavioral safety of nelonemdazK compared to selfotel,
an NMDA antagonist, in ischemic stroke patients

|  |  | Clinical study for nelonemdazK | | Clinical studies for selfotel | |
|---|---|---|---|---|---|
|  |  | Drug (n = 179) | Placebo (n = 59) | selfotel (n = 281) | Placebo (n = 286) |
| Number (%) of subjects showing abnormal behavior | Hallucination | 0 (0%) | 0 (0%) | 59 (21%)* | 13 (5%) |
|  | Paranoia | 0 (0%) | 0 (0%) | yes | no |
|  | Delirium | 0 (0%) | 0 (0%) | yes | no |
|  | Agitation | 4 (2%) | 0 (0%) | 101 (36%)* | 39 (1%) |
|  | Confusion | 0 (0%) | 0 (0%) | 46 (16%)* | 16 (6%) |
|  | Stupor | 1 (1%) | 1 (2%) | 12 (4.3%)* | 0 (0%) |

Clinical trials of selfotel for ischemic stroke patients (Grotta et al, 1995; Davis et al, 2000)

TABLE 4

Formulation process of nelonemdazK drug
product—Formulation of nelonemdazK for injection

| Ingredient | Amount per Unit Strength 250 mg | | 12,000 Units Strength 250 mg | | Function |
|---|---|---|---|---|---|
|  | Per Unit | Percentage (%) | Amount added | Percentage (%) |  |
| nelonemdaz KOH | 250 mg | 8.09 | 3.0 kg | 8.09 | API |
| KOH | Add KOH to adjust pH to 8-10 |  | Add KOH to adjust pH to 8-10 |  | pH adjustment |
| Water for Injection (WI) | Add qualified sterile water to 3 ml |  | Add qualified sterile water to 36 L |  | Diluent |
| Total | 3.09 g | 100 | 37.08 Kg | 100 |  |

EXAMPLES

Example 1: Safety of nelonemdazK in Normal Rats and Healthy Humans

1. Purpose

NMDA receptor antagonists produce unwanted side effects involving neurotoxicity and psychotic symptoms. We have studied to examine if nelonemdazK, an NR2B-selective NMDA receptor antagonist, would be safe in normal rats and healthy humans.

2. Toxicity of NMDA Receptor Antagonists

Systemic administration of NMDA antagonists such as MK-801, phencyclidine, and ketamine were reported to cause neurotoxic side effects and neuronal death in rodents (Olney et al, 1989). In humans, NMDA receptor antagonists can induce serious side effects like hallucinations, paranoid, agitation, and catatonia a transient psychotomimetic mental state. MK-801, a noncompetitive NMDA receptor antagonist, was withdrawn from further development due to neuropsychological adverse events as well as neurotoxicity (Ginsberg, 2008). Administration of aptiganel, a non-competitive NMDA antagonist, to healthy humans caused hallucinations, paranoia, catatonia, euphoria, disinhibition, and psychomotor retardation (Muir et al., 1994; Muir et al., 1995). Intravenous injection of 2-3 mg/kg selfotel (CGS19755), a competitive NMDA receptor antagonist, produced transient side effects including sedation, dizziness, motion sickness with disorientation, and nausea without abnormal findings on neurological examination (Grotta et al, 1995). However, administration of 1 mg/kg selfotel showed hallucinations, paranoia, agitation, confusion, and delirium in stroke patients (Grotta et al., 1995; Davis et al., 2000).

3. Comparison of MK-801 and nelonemdazK for Neurotoxicity and Abnormal Behavior (Table 1a & 1b):

Adult rats (n=96) were euthanized at various time points (0, 1, 3, 5, or 9 day(s) following a single dose administration of MK-801 (1 or 10 mg/kg, IP), nelonemdazK (200 mg/kg, IV over 15 min), or vehicle. Brain sections were stained using de Olmos' amino-cupric-silver technique to examine neurodegeneration as described (Fix et al, 1996).

All animals treated with 1 mg/kg or 10 mg/kg MK-801 revealed neuronal death in various brain areas including retrosplenial cortex, entorhinal cortex, and hippocampal formation as reported by Olney et al. (Table 1a). Such neuronal injury was not observed in male and female rats treated with 200 mg/kg nelonemdazK. Administration of MK-801 also produced abnormal behaviors including ataxia and decreased activity in male and female rats, which was not observed in animals treated with nelonemdazK (Table 1b). This implies that nelonemdazK does not cause neurotoxicity and psychotic symptoms often produced by NMDA antagonists.

4. Behavioral Safety of nelonemdazK Compared to Aptiganel, an NMDA Antagonist, in Healthy Volunteers (Table 2)

NMDA receptor antagonists were reported to produce serious side effects in healthy humans. In a phase 1 study for 94 healthy volunteers, administration of aptiganel produced 1995; table 2), In two phase I studies for 165 healthy volunteers co psychotic symptoms such as hallucinations, paranoia, and catatonia (Muir et al., 1994 and inducted in the US and China, single administration of nelonemdazK maximally up to 6,000 mg did not show serious psychiatric and neurological adverse events such as hallucinations, paranoia, catatonia, agitation, and confusion (table 2). Moreover, multiple administration of nelonemdazK maximally up to 6,000 mg (initial 1500 mg IV infusion and additional 9 IV infusions of 500 mg, twice a day) for 5 days did not produce any psychotic symptoms.

Example 2: Behavioral Safety of nelonemdazK Compared to Selfotel, an NMDA Antagonist, in Ischemic Stroke Patients (Table 3)

NMDA receptor antagonists can cause adverse events in ischemic stroke patients. In clinical trials for ischemic stroke patients, some of 281 patients administered with selfotel revealed psychotic symptoms such as hallucination, paranoia, and delirium (Davis et al, 2000; Grotta et al, 1995: table 3). However, none of ischemic stroke patients showed such psychotic symptoms in 179 ischemic stroke patients treated with nelonemdazK maximally up to 6,000 mg for 5 days.

Example 3: Prevention of a Hemolytic Drug-Induced Hemorrhagic Transformation 1. tMCAO (transient Middle Cerebral Artery Occlusion) Animal Model Male Sprague-Dawley rats (300-350 g; 15-16 animals/group) were anesthetized with chloral hydrate (400 mg/kg, IP) and the anesthesia was sustained for about 1.5 h during the procedure. The rectal temperature was recorded and maintained at 37.0-37.5° C. using a rectal probe and homoeothermic blanket controlled by a temperature control unit (Letica Scientific Instruments). Occlusion of the MCA was done according to the previous report (Gwag et al., 2007). Briefly, the right common carotid artery, external carotid artery (ECA), and internal carotid artery (ICA) were exposed. A length of 4-0 monofilament nylon suture (17 mm, pre-coated with silicone) with its tip rounded by heating near a flame was advanced from the lumen of the ICA until it blocked the origin of the middle cerebral artery (MCA). The suture remained for 3 h and was withdrawn for reperfusion. After 24 h, the brain was removed immediately, placed in the fixative for 15 min, and used for further analysis.

2. rt-PA-Induced Hemorrhagic Transformation Model

Male Sprague-Dawley rats (340-380 g) were anesthetized with chloral hydrate (400 mg/kg, IP). The animals received intracortical injection of rt-PA (0.66 mg/kg; total 30 mole) coordinated with 2.6 mm posterior, 5.4 mm lateral, and 3.8 mm from bregma at a flow rate of 0.5 µL/min using a infusion pump and Hamilton syringe. After the end of infusion, the syringe was removed from the cortex and nelonemdazK (30 mg/kg) was administered through femoral vein for 5 min (3 mg/mL; 10 mL/kg). Six hours later, the rats were anesthetized and intravenously administered with 4% Evans blue solution. Twenty minutes later, the rats were perfused transcardially first with saline and next with 4% paraformaldehyde. The brain was removed immediately and placed in the fixative for 15 min and scanned for evaluation of extravasation area of Evans blue to indirectly measure rt-PA-induced hemorrhagic transformation which occurs as a result of the breakdown of the blood-brain barrier (Jiang et al., 2018). To evaluate brain damage volume, the brain tissues were stored in 4% paraformaldehyde for 3 days and then processed overnight for paraffin embedding and cresyl violet staining. The extravasation area was measured by TINA imaging system (KAIST, Korea).

3. Prevention of rt-PA-Induced Hemorrhagic Transformation Following 3-h Occlusion of Middle Cerebral Artery in Adult Rats (FIG. 1A)

Animals received transient focal cerebral ischemia for 3 h as described above with intravenous administration of 10 mg/kg rt-PA or 10 mg/kg rt-PA plus 30 mg/kg nelonemdazK after reperfusion. rt-PA (10 mg/kg) dissolved in water for injection (6 mg/mL; 5 mL/kg) was injected through femoral vein over 20 min from 5 min after reperfusion. NelonemdazK (30 mg/kg) dissolved in saline (6 mg/mL; 5 mL/kg) was injected through femoral vein over 5 min immediately after the end of rt-PA infusion. (Upper panel) NelonemdazK prevented hemorrhage produced in the brain of animals treated with rt-PA after 3-h tMCAO. (Lower panel) Administration of nelonemdazK significantly reduced the rate of hemorrhagic transformation evolving in animals treated with rt-PA following 3-h tMCAO ($p<0.05$ by Fisher's exact test).

Figure 1B:
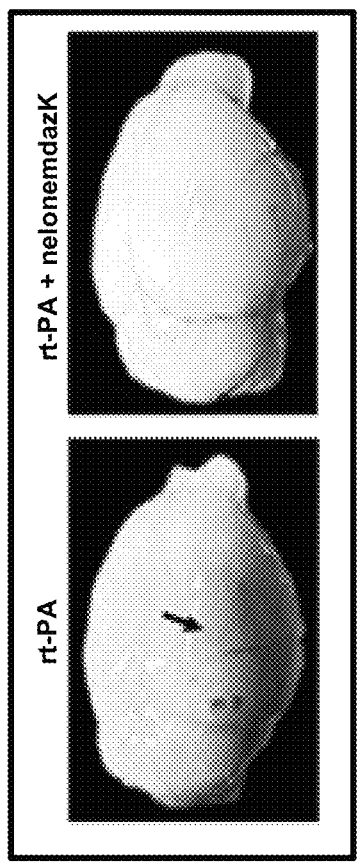
FIG. 1B: Effects of tPA and nelonemdaz on acute brain injury at 24 h after embolic stroke in mice. Upper and lower panels show that nelonemdazK prevents hemorrhagic transformation in the brain of adult mice treated with rt-PA after embolic stroke.
Figure 1B:
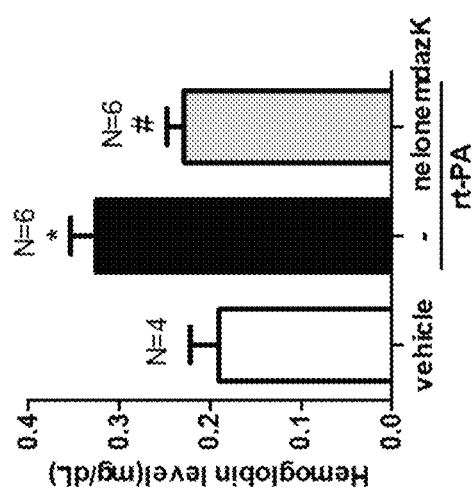

4. NelonemdazK Prevents Adverse Events Evolving in Mice Treated with rt-PA after Embolic Stroke (FIG. 1B).

Embolic stroke was induced by injection of blood clot into the right internal carotid artery of mice. Animals received intravenous administration of saline, 10 mg/kg rt-PA, or 10 mg/kg rt-PA plus nelonemdazK through femoral vein at 4.5 hours after embolic stroke. rt-PA was dissolved in water and injected over 20 min. NelonemdazK was dissolved in saline and injected over 5 min immediately after rt-PA infusion. Hemorrhage and brain injury were analyzed 24 hours after embolic stroke.

Upper panel: Delayed rt-PA administration causes hemorrhage in the ischemic region of mice subject to embolic stroke compared to vehicle (saline) treatment that does not produce hemorrhage after embolic stroke. Lower panel: Administration of nelonemdazK significantly reduced the levels of hemoglobin as well as hemorrhage in the ischemic brain region of mice treated with rt-PA after embolic stroke (Mean±S.E.M., *$p<0.05$ versus saline and #$p<0.05$ versus rt-PA plus nelonemdazK using unpaired-t tests).

Figure 1C:
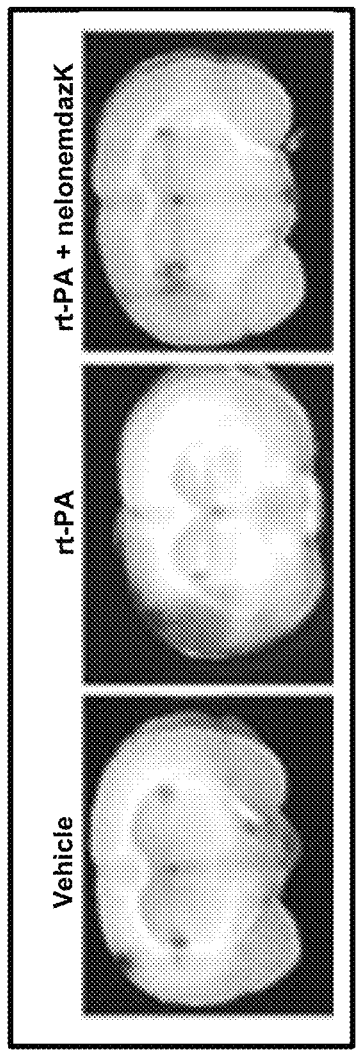
FIG. 1C: Prevention of rt-PA-induced hemorrhagic transformation in normal adult rats. Upper and lower panels show prevention of rt-PA-induced hemorrhagic transformation in normal adult rats.
Figure 1C:
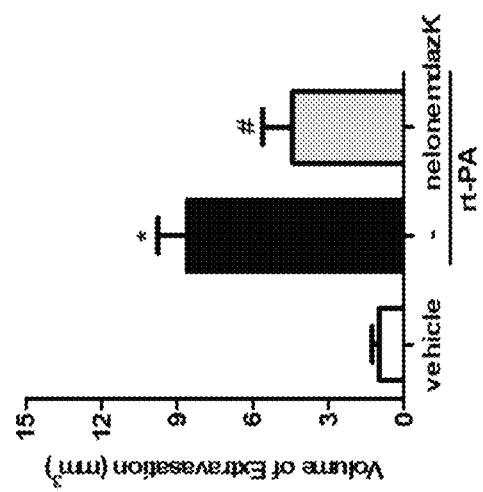

5. Prevention of Rt-PA-Induced Hemorrhagic Transformation in Normal Adult Rats (FIG. 1C)

Animals received the intracortical injection of 0.66 mg/kg rt-PA that was followed by subsequent IV administration of vehicle or 30 mg/kg nelonemdazK 5 min later. Hemorrhagic transformation was investigated by analyzing extravasation of Evans blue dye at 6 h after rt-PA. (Upper panel) Compared to the sham control group, administration of rt-PA produced hemorrhagic transformation evident by extravasation of Evans blue, which was prevented by subsequent treatment with nelonemdazK. (Lower panel) Compared to the vehicle-treated group, the administration of nelonemdazK significantly reduced the volume of Evans blue extravasation following rt-PA injection (value=Mean±S.E.M., n=3 for sham and 6 for rt-PA-treated groups; $p<0.05$ using one-way ANOVA and Tukey test).

Figure 1D:
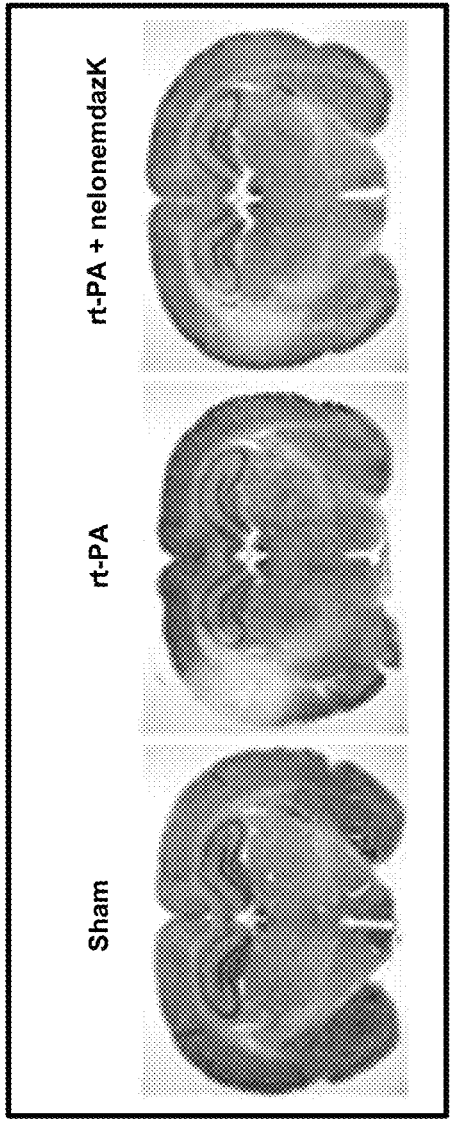
FIG. 1D: Prevention of rt-PA-induced brain injury in normal adult rats. Upper and lower panels show prevention of rt-PA-induced brain injury in normal adult rats.
Figure 1D:
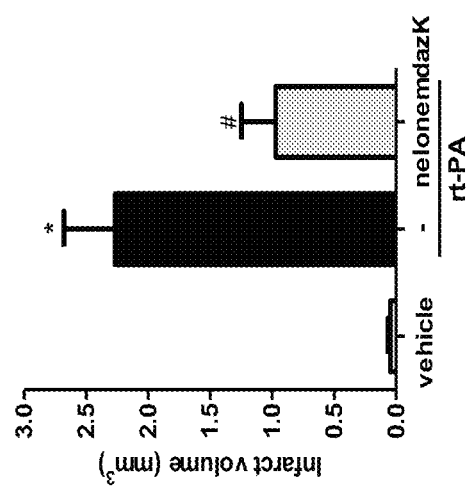

6. Prevention of rt-PA-Induced Infarct Volume in Normal Adult Rats (FIG. 1D)

Animals received sham operation or the intracortical injection of 0.66 mg/kg rt-PA, alone or with the subsequent intravenous administration of vehicle or 30 mg/kg nelonemdazK. Animals were sacrificed 6 h later and infarct volume was analyzed after staining brain sections with cresyl violet. (Upper panel) Photographs of brain sections stained with cresyl violet. Note brain lesion following the intracortical injections of rt-PA that was prevented by the administration of nelonemdazK. (Lower panel) Quantitation of infarct volume (Mean±S.E.M., n=3 for sham and 6 for rt-PA-treated groups) by summation of lesion areas in brain sections. Compared to the vehicle-treated group, the administration of nelonemdazK significantly reduced infarct volume evolving 6 h after rt-PA, using one-way ANOVA and Tukey test.

The studies above demonstrate that the intravenous administration of nelonemdazK reduces rt-PA-induced hemorrhagic transformation and brain damage.

Example 4: Beneficial Effects of nelonemdazK for Acute Ischemic Stroke Patients Receiving a Thrombolytic Drug 1. A Phase II Clinical Trial Design of nelonemdazK for Acute Ischemic Stroke Patients in China (ENIS Trial)

The ENIS trial was to examine efficacy as well as safety of the intravenous infusions of nelonemdazK for acute ischemic stroke patients (35-80 years old) receiving at least one kind of thrombolytic drugs including rtPA or urokinase within 8 hours of onset. A total of 238 patients were enrolled for the ENIS trial and allocated randomly in a double-blinded manner to one of 4 groups for the intravenous infusions of test drugs as follows: (Group A) placebo [0.9% normal saline], (Group B) 2,750 mg nelonemdazK for 5 days [500 mg for $1^{st}$ infusion followed by $2^{nd}$-$10^{th}$ infusions approximately at 12 h intervals (250 mg for each infusion)], (Group C) 5,250 mg nelonemdazK for 5 days [750 mg for $1^{st}$ infusion followed by $2^{nd}$-$1^{st}$ infusions approximately at 12 h intervals (500 mg for each)], and (Group D) 6,000 mg nelonemdazK for 5 days [1500 mg for $1^{st}$ infusion followed by $2^{nd}$-$1^{st}$ infusions approximately at 12 h intervals (500 mg for each)]. Acute ischemic stroke patients due to occlusion in internal carotid artery system within 8 hours of onset were enrolled. Patients with The National Institutes of Health Stroke Scale (NIHSS; range 0-42, with higher scores indicating greater stroke severity) scores of 4 to 22 and limb weakness including motor arm or motor leg score ≥2 of NIHSS were included. All the patients received at least one kind of thrombolytic therapy before treatment of any study drug.

Figure 2A:
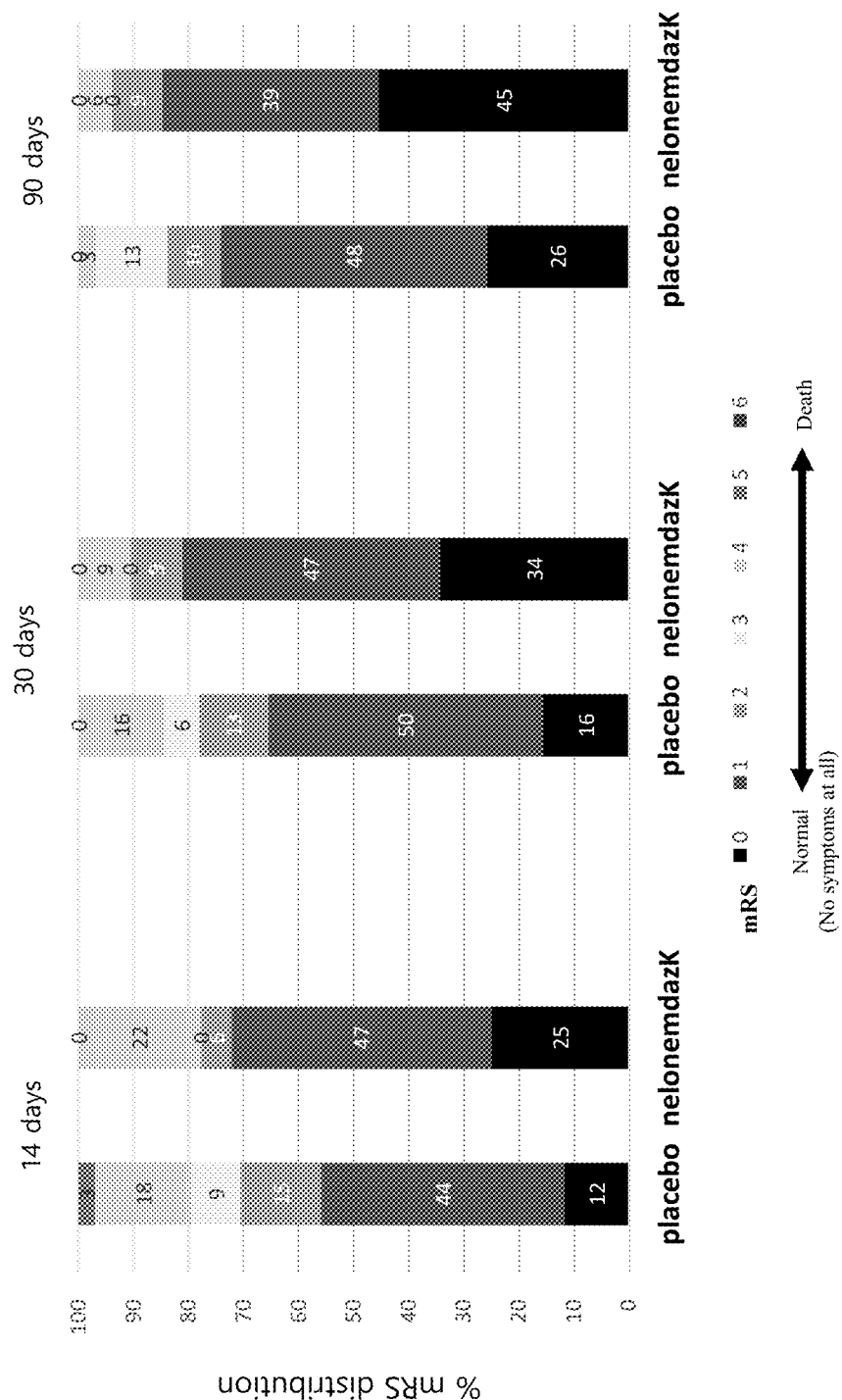
FIG. 2A: % Change of mRS distribution at 14, 30, and 90 days after drug treatment in patients with NIHSS score 6-24 at baseline (Day 0).
Figure 2B:
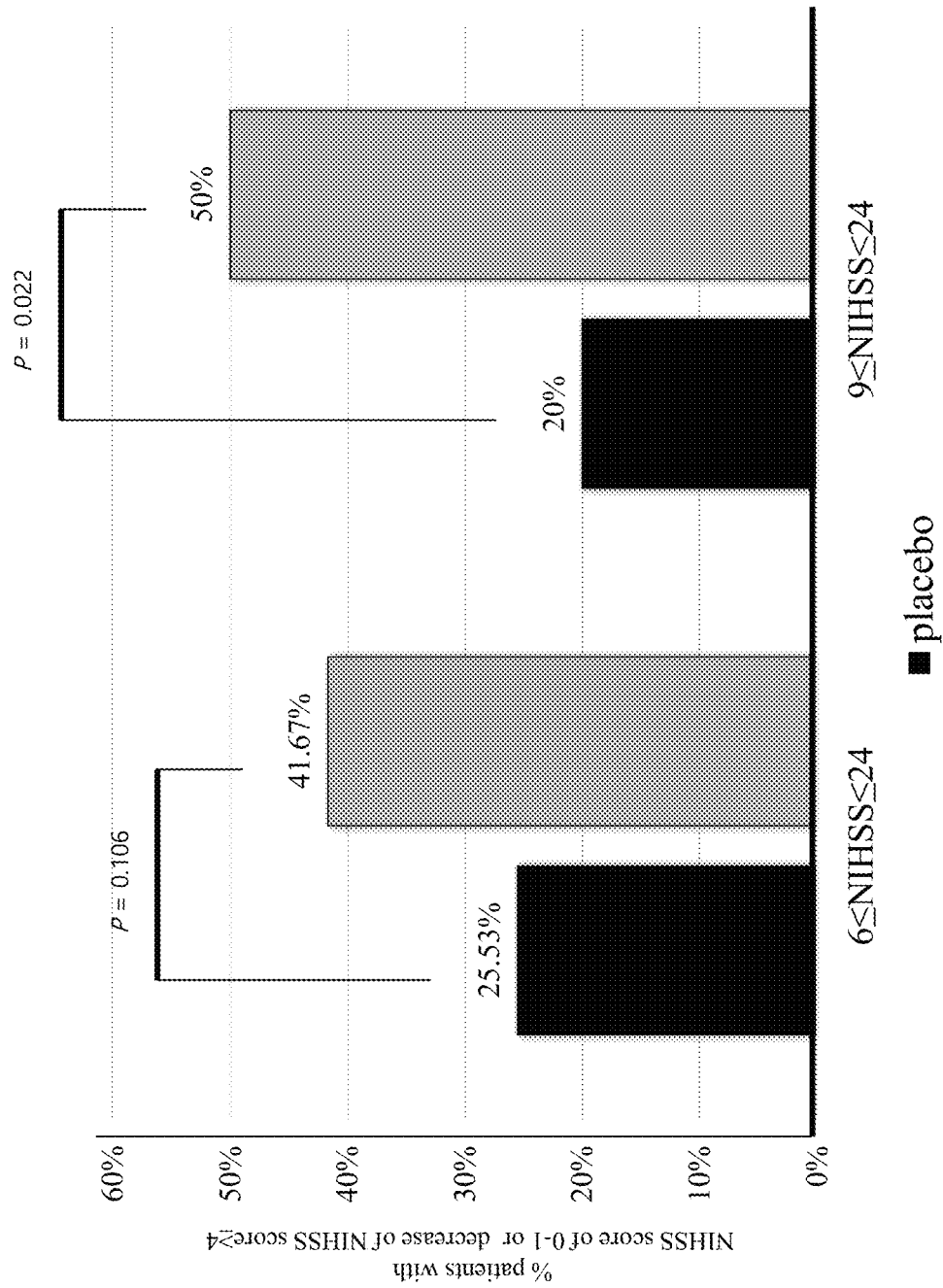
FIG. 2B: The percentage of patients showing NIHSS score of 0-1 or decrease of NIHSS score≥4 at 14 days after drug treatment in patients with the baseline (Day 0) NIHSS score of 6-24 or 9-24.

2. Efficacy of nelonemdazK in "ENIS" Trial (FIG. 2A and FIG. 2B)

The modified Rankin Scale (mRS; 0=no symptoms, 1=no significant disability, 2=slight disability, 3=moderate disability, 4=moderately severe disability, 5=Severe disability, 6=death] was used to analyze efficacy of nelonemdazK for acute ischemic stroke patients with the baseline NIHSS score 6-24. Shift analysis of mRS at 14, 30, and 90 days from drug treatment showed that administration of 6,000 mg nelonemdazK increased the percentage of mRS 0-2 (functional independence) compared with the placebo-treated group (FIG. 2A). The ratio of mRS 0 (no symptoms at all) corresponding to near complete recovery after stroke was 12% at 14 days, 16% at 30 days, and 26% at 90 days after placebo treatment, which was further increased to 25%, 34%, and 45%, respectively, after nelonemdazK treatment for ischemic stroke patients.

The beneficial effects of nelonemdazK were further observed by analyzing "the ratio of patients with NIHSS score of 0-1 or decrease of NIHSS score≥4 (=the good recovery ratio)" at 14 days after drug treatment. For the acute ischemic stroke patients with the baseline NIHSS score 6-24, the good recovery ratio in the group treated with placebo (N=34) or 6,000 mg nelonemdazK (N=36) was 25.53% and 41.67% (p=0.106 between groups, chi-square test), respectively (FIG. 2B). For the moderate to severe patients with the baseline NIHSS score 9-24, the good recovery ratio was 20% for the placebo-treated group (N=3), which was significantly (p=0.022 between groups) further increased to 50% for the nelonemdazK-treated group (N=9). This implies that the beneficial effects of nelonemdazK are better for moderate to severe (NIHSS score 6) ischemic stroke patients than mild (NIHSS score 5) patients.

Example 5: Safety and Beneficial Effects of nelonemdazK for Acute Ischemic Stroke Patients Receiving Endovascular Thrombectomy (SONIC Trial)

1. A Phase II Clinical Trial Design and Statistical Analysis of nelonemdazK for Acute Ischemic Stroke Patients Receiving Endovascular Thrombectomy with or without rt-PA The SONIC trial was to examine efficacy and safety of the intravenous infusions of nelonemdazK for acute ischemic stroke patients (adults 19) receiving endovascular thrombectomy with or without rt-PA within 8 hours of onset as described (Hong et al., 2018). A total of 209 patients were enrolled for the SONIC trial and allocated randomly in a double-blinded manner to one of 3 groups for the intravenous infusions of test drugs as follows: (Group A) placebo [0.9% normal saline], (Group B) 2,750 mg nelonemdazK for 5 days [500 mg for $1^{st}$ infusion followed by $2^{nd}$-$10^{th}$ infusions approximately at 12 h intervals (250 mg for each infusion)], and (Group C) 5,250 mg nelonemdazK for 5 days [750 mg for $1^{st}$ infusion followed by $2^{nd}$-$10^{th}$ infusions approximately at 12 h intervals (500 mg for each)].

Acute ischemic stroke patients due to occlusion in carotid internal carotid artery system within 8 hours of onset were enrolled. Enrolled patients presented the National Institutes of Health Stroke Scale (NIHSS: range 0-42, with higher scores indicating greater stroke severity) scores 8 and Alberta stroke program early CT score (ASPECTS: a 10-point quantitative topographic CT scan score used in patients with middle cerebral artery (MCA) stroke, with lower scores indicating larger cerebral infarction)≥6.

For statistical analysis, Cochran-Mantel-Haenszel (CMH) chi-square test was conducted to compare distribution and ratio of mRS scores for each group at 1, 4, and 12 weeks after drug treatment. Ordinal logistic regression was applied with multivariate analysis controlling confounding variables that may cause difference between the groups in participating institutions and baseline scores. In addition, generalized estimating equation (GEE) analysis was conducted to compare the changes between groups in mRS scores measured at 1, 4, and 12 weeks after drug treatment. For the analysis of the Barthel Index score and adverse events, chi-square test or Fisher exact test was conducted to compare difference between groups at 1, 4, and 12 weeks after drug treatment.

Figure 3A:
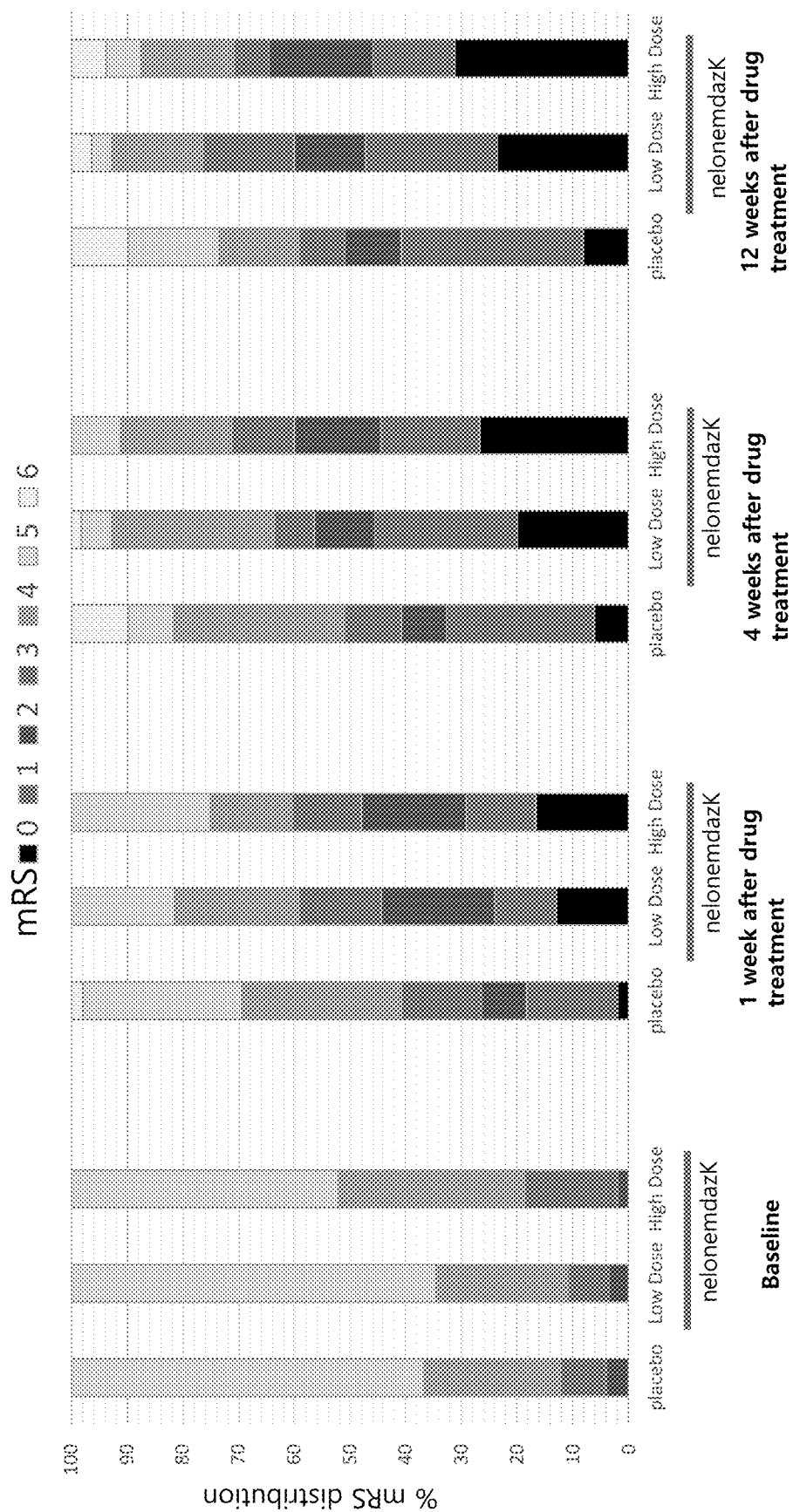
FIG. 3A: The distribution of mRS at 1, 4, and 12 weeks before (Baseline) and after drug treatment.
Figure 3B:
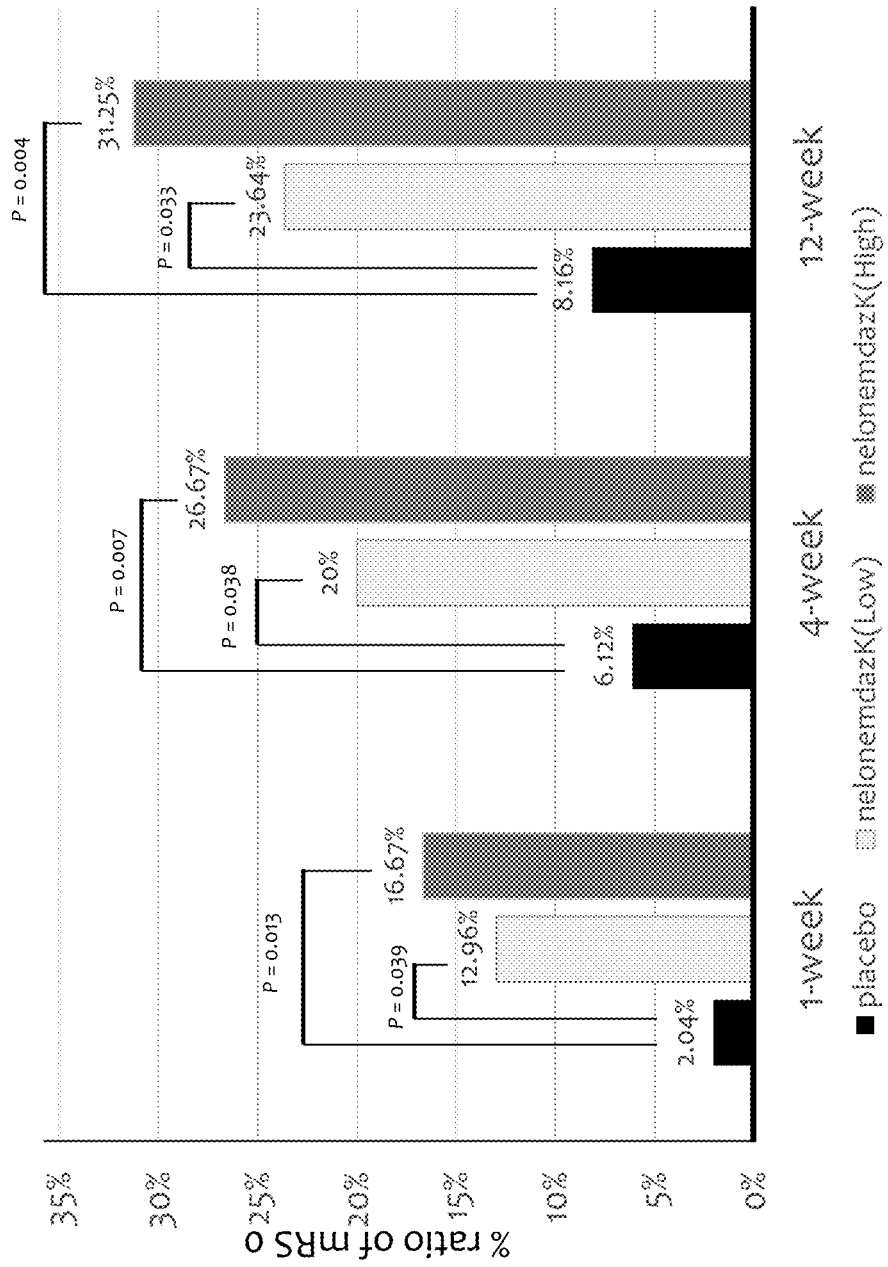
FIG. 3B: The ratio of mRS 0 at 1, 4, and 12 weeks after drug treatment.
Figure 3C:
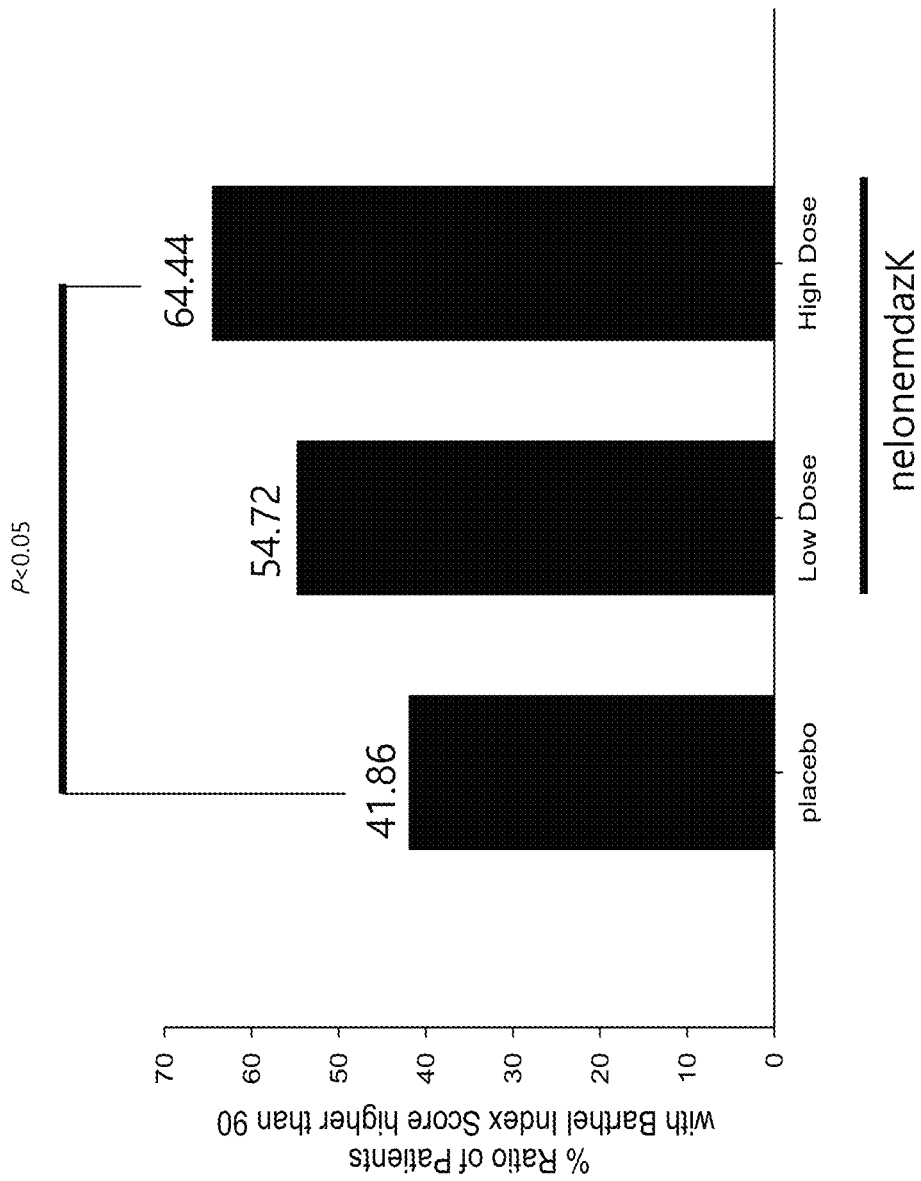
FIG. 3C: The ratio of patients showing Barthel Index score higher than 90 at 12 weeks after drug treatment.

2. Efficacy and Safety of nelonemdazK in "SONIC" Trial (FIG. 3A to FIG. 3C)

Acute ischemic stroke patients who presented the baseline NIHSS score≥8 and the mRS distribution of 2-5 were enrolled for the SONIC trial. Out of a total of 209 patients, 152 patients successfully completed procedures including drug treatment for 5 days and scheduled analysis over 12 weeks after drug treatment according to the clinical protocol approved by Korea Ministry of Food and Drug Safety. Placebo group (N=49) who received endovascular thrombectomy showed increase in the ratio of mRS 0-2 (functional independence) or 0 (no symptoms at all) compared to the baseline over the next 12 weeks, suggesting improved functional recovery. Compared to the placebo, the ratio of mRS 0-2 or 0 was further increased in patients treated with low dose (2,750 mg, N=55) or high dose (5,250 mg, N=48) nelonemdazK (FIG. 3A). The shift analysis implies that administration of nelonemdazK reduces disability in acute stroke patients treated with endovascular thrombectomy.

The ratio of mRS 0 (no symptoms at all) was increased in all treated groups gradually from baseline to 12 weeks over time. The ratio of mRS 0 without any symptoms was 2.04% in patients treated with placebo for 1 week, which was significantly increased to 12.96% (p=0.04) and 16.67% (p=0.01) in groups treated with low or high dose nelonemdazK for 1 week, respectively (FIG. 3B). At 4 weeks after drug treatment, the mRS 0 ratio was further increased to 20% (p=0.04) in low dose nelonemdazK-treated group and 26.67% (p=0.007) in high dose nelonemdazK-treated group compared to 6.12% in the placebo-treated group. At 12 weeks after drug treatment, increase in the mRS 0 ratio was significant in low (23.64%, p=0.03) and high (31.25%, p=0.004) dose group compared to the placebo group (8.16%).

Beneficial effects of nelonemdazK were confirmed by an analysis using the Barthel Index (BI) that measures the activities of daily living and mobility with a total score of 0 (totally dependent) and 100 (completely independent). All stroke patients were totally dependent (BI=0) before drug treatment. At 12 weeks after drug treatment, the ratio of patients with BI score higher than 90 was 41.86% in placebo-treated group, which was increased to 54.72% in low dose nelonemdazK-treated group and further significantly to 64.44% (p<0.05) in high dose nelonemdazK-treated group (FIG. 3C).

For safety analysis, 208 patients (99.52%) out of 209 patients enrolled for the SONIC trial were analyzed over 12 weeks after drug treatment. The mortality rate for placebo group (N=70), low dose nelonemdazK group (N=71), and high dose nelonemdazK group (N=67) was 8.57% (6/70), 4.23% (3/71), and 4.48% (3/67), respectively. There is no difference between placebo and nelonemdazK-treated group in the occurrence of adverse events and serious adverse events. There are no drug-related adverse events. Thus, intravenous administration of nelonemdazK up to 5,250 mf for 5 days was safe in acute ischemic stroke patients treated with endovascular thrombectomy with or without rt-PA.

Example 6: Superiority of a Single Molecule with Dual NMDA Antagonist and AntiOxidant Properties to Concurrent Administration of an NMDA Antagonist and an AntiOxidant Administration of a single molecule with dual NMDA antagonist and antioxidant properties guarantees the co-delivery of these activities at the single cell and even molecular level. Synergy between NMDA antagonism and reduction of harmful free radicals at the single cell level might increase neuroprotective efficacy or reduce Olney cytotoxicity evolving after administration of MNDA antagonists. Modulation of NMDA receptors at the redox site could conceivably further contribute to nelomemdaz' favorable efficacy/safety profile in ischemic stroke patients receiving recanalization therapy and relevant neurological diseases.

Example 7: Optimization of Drug Product Formulation of nelonemdazK (Table 4)

As the drug product (nelonemdazKL) of nelonemdazK used for the phase I clinical study showed precipitation on occasion after reconstitution prior to administration to human subjects, the present inventors developed a new drug product through optimization process of nelonemdazK. The new drug product named nelonemdazKWL is produced by formulation of nelonemdazK and freeze-drying cycle. In brief, nelonemdazK was dissolved in nanopure water, added with KOH to adjust pH to 9.2-9.7, and then filtered through sterile filters (Table 4). The resulting nelonemdazK solution was lyophilized through 3 step-process consisting of pre-freezing, $1^{st}$ drying, and $2^{nd}$ drying all under $N_2$ gas to minimize the air exposure time. The new drug product is named as "nelonemdazKWL" and characterized by good finer cakes with near white color and without needle-shaped crystals. NelonemdazKWL is reconstituted in sterile water for injection without producing precipitation.

The precipitation problem of nelonemdazKL can be resolved by other methods: (1) reformulating with new buffering agent such as (tris)hydroxymethyl]aminomethane [THAM, $(HOCH_2)_3CNH_2$], borate, carbonate, etc. rather than sterile water for injection (SWFI); (2) changing reconstitution vehicle to THAM or bicarbonate, and changing the vial stopper to a coated stopper to reduce loss of DEA (3) Reconstitution of sterile API (Active Pharmaceutical Ingredients) using THAM buffer (4) reconstitution of sterile API using DEA-Mannitol Buffer.

Example 8: Ischemic Stroke Treated with Thrombolytic Drugs

Stroke is a disease in which a blood vessel to the brain is either blocked by a clot or bursts. rt-PA is a standard thrombolytic therapy for acute ischemic stroke patients according to 2018 American Heart Association (AHA)/American Stroke Association (ASA) Guidelines for the early management of patients with acute ischemic within 4.5 hours of symptomatic onset until 2015 [Benjamin et al, 2018; The National Institute of Neurological Disorders and Stroke rt-PA Stroke Study Group, 1995]. Clinical benefits were observed when intravenous rt-PA was administered to ischemic stroke patients within 6 hours of symptomatic onset (Fugate and Rabinstein, 2014). As shown above, the present invention provides evidence that nelonemdazK provides beneficial effects for acute ischemic stroke patients receiving recanalization therapy through one of thrombolytic drugs. The thrombolytics can include rt-PA, modified rt-PA, urokinase, and other suitable thrombolytic drugs.

In some of the embodiments, nelonemdazK is administered to ischemic stroke patients receiving recanalization therapy at a total dose of 6,000 mg for 5 days. For example, 1st 1500 mg, then 2nd~10th 500 mg each around at 12 h intervals, all via IV infusion over 30 min. Alternatively, nelonemdazK is administered to ischemic stroke patients receiving recanalization therapy at a total dose of 5,250 mg. For example, 1st 750 mg, then 2nd~10th 500 mg around at 12 h dose for 5 days.

Example 9: Acute Ischemic Stroke Patients Receiving Endovascular Thrombectomy Endovascular thrombectomy with or without a thrombolytic drug has been used as a standard therapy for acute ischemic stroke patients. The present invention provides evidence that nelonemdaz improves neurological function for acute ischemic stroke patients receiving endovascular thrombectomy with or without rt-PA within 8 hours of onset. In addition, nelonemdaz reduced adverse events shown in ischemic stroke patients receiving endovascular thrombectomy with or without rt-PA. The thrombolytics used with endovascular thrombectomy can include rt-PA, modified rt-PA, urokinase, and other suitable thrombolytic drugs. The endovascular thrombectomy device can include Trevo, Solitaire FR, Penumbra, and other suitable devices.

Example 10: Combination Therapy with Thrombolytic Drugs

Thrombolytic drugs including rt-PA and modified rt-PA have been used to treat venous thromboembolism, acute myocardial infarction, occluded catheters, pediatric pleural effusions, and prosthetic valve thrombosis (Wandell et al., 2019; Gurwitz et al., 1998; Blaney et al, 2006; Biteker et al, 2015). However, such thrombolytic drugs can produce serious adverse events such as intracranial hemorrhage.

Nelonemdaz can be applied to prevent the adverse events evolving after administration of thrombolytic drugs.

Example 11: Combination Therapy with Coronary Thrombectomy

Coronary artery thrombosis can cause myocardial infarction. Thrombolytic therapy has been used for the treatment of coronary artery thrombosis. Blood flow to the ischemic myocardium is restored following coronary artery thrombectomy but such restored blood flow may result in reperfusion injury to the myocardium, Nelonemdaz can be used to treat the reperfusion injury resulting from the coronary artery thrombectomy.

As described hereinbefore, tetrafluorobenzyl compounds, their pharmaceutically acceptable salts, and pharmaceutical compositions containing the same as the effective component can be used to treat acute ischemic stroke patients receiving a thrombolytic drug, acute ischemic stroke patients receiving endovascular thrombectomy with or without treatment of a thrombolytic therapy, patients receiving a thrombolytic therapy, and acute myocardial infarction receiving coronary artery thrombectomy.

REFERENCES

1. Balami J. S. et al., Complications of endovascular treatment for acute ischemic stroke: Prevention and management. Int J Stroke. 2018; 13(4):348-361.
2. Bang O. Y. et al., Dreaming of the future of stroke: translation of bench to bed. Precis Future Med. 2017; 1(4):143-151.
3. Benjamin, E. J., et al., Heart Disease and Stroke Statistics-2018 Update: A Report From the American Heart Association. Circulation, 2018; 137(12):e67-e492.
4. Biteker M. et al., Treatment of prosthetic valve thrombosis: Current evidence and future directions. J Clin Med Res. 2015; 7(12):932-936.
5. Blaney M. et al., for CAPS Investigators. Alteplase for the treatment of central venous catheter occlusion in children: results of a prospective, open-label, single-arm study (the Cathflo Activase Pediatric Study). J Vasc Interv Radiol. 2006; 17(11, pt 1):1745-1751.
6. Chamorro Á., Neuroprotectants in the era of reperfusion therapy. J Stroke. 2018; 20(2):197-207.
7. Chamorro Á. et al., Planas A M. Neuroprotection in acute stroke: targeting excitotoxicity, oxidative and nitrosative stress, and inflammation. Lancet Neurol. 2016; 15:869-81.
8. Cho S. I. et al., Neu2000, an NR2B-selective, moderate NMDA receptor antagonist and potent spin trapping molecule for stroke. Drug News Perspect. 2010; 23:549-56.
9. Davis S. M. et al., Selfotel in acute ischemic stroke: possible neurotoxic effects of an NMDA antagonist. Stroke. 2000; 31(2):347-54.
10. Dong Q. et al. The Chinese Stroke Association scientific statement: intravenous thrombolysis in acute ischaemic stroke. Stroke and Vascular Neurology 2017; 2(3):147-159.
11. Farber N. B. et al., Receptor mechanisms and circuitry underlying NMDA antagonist neurotoxicity. Mol Psychiatry. 2002; 7(1):32-43.
12. Feigin V. L. et al., Global burden of stroke and risk factors in 188 countries, during 1990-2013: a systematic analysis for the global burden of disease study 2013. Lancet Neurol. 2016; 15(9):913-924.
13. Fix A. S. et al., Integrated evaluation of central nervous system lesions: Stains for neurons, astrocytes, and microglia reveal the spatial and temporal features of MK-801-induced neuronal necrosis in the rat cerebral cortex. Toxicol Pathol. 1996; 24(3):291-304.
14. Fugate J. and Rabinstein A. A. Update on intravenous recombinant tissue plasminogen activator for acute ischemic stroke. Mayo Clin Proc. 2014; 89(7):960-72.
15. Ginsberg M. D., Neuroprotection for ischemic stroke: Past, Present, and Future. Neuropharmacology. 2008; 55(3): 363-389.
16. Grotta J. et al., Safety and tolerability of the glutamate antagonist CGS 19755 (Selfotel) in patients with acute ischemic stroke. Results of a phase IIa randomized trial. Stroke. 1995; 26(4):602-5.
17. Gurwitz J. H. et al., Risk for intracranial hemorrhage after tissue plasminogen activator treatment for acute myocardial infarction. Ann Intern Med. 1998; 129(8): 597-604.
18. Gwag B. J. et al., Marked prevention of ischemic brain injury by Neu2000, an NMDA antagonist and antioxidant derived from aspirin and sulfasalazine. J Cereb Blood Flow Metab. 2007; 27:1142-51.
19. Hishida A., Clinical analysis of 207 patients who developed renal disorders during or after treatment with edaravone reported during post-marketing surveillance. Clin Exp Nephrol. 2007; 11(4):292-296.
20. Hong J. M. et al., Safety and Optimal Neuroprotection of neu2000 in acute Ischemic stroke with reCanalization: study protocol for a randomized, double-blinded, placebo-controlled, phase-II trial. Trials 2018; 19:375.
21. Jiang X et al., Blood-brain barrier dysfunction and recovery after ischemic stroke. Prog Neurobiol. 2018; 163-164:144-171.
22. Minnerup J. et al. Neuroprotection for stroke: current status and future perspectives. Int J Mol Sci. 2012; 13(9):11753-72.
23. Muir K. W. et al., Clinical Pharmacology of CNS 1102 in Volunteers. Ann N Y Acad Sci. 1995; 765:279-89; discussion 298.
24. Muir K. W. et al., Pharmacological effects of the non-competitive NMDA antagonist CNS 1102 in normal volunteers. Br J Clin Pharmacol. 1994; 38(1):33-8.
25. Muir K. W. and Lees K. R., Excitatory amino acid antagonists for acute stroke. Cochrane Database of Systematic Reviews. 2003; Issue 3. Art. No.: CD001244.
26. Nogueira R. G. et al, Thrombectomy 6 to 24 Hours after Stroke with a Mismatch between Deficit and Infarct. N Engl J Med. 2018; 378(1):11-21.
27. Olney J. W. et al., Pathological changes induced in cerebrocortical neurons by phencyclidine and related drugs. Science. 1989; 244(4910):1360-1362.
28. Orgogozo et al., Efficacy and Safety of Memantine in Patients With Mild to Moderate Vascular Dementia. Stroke. 2002; 33:1834-1839.
29. Powers W. J. et al., Guidelines for the early management of patients with acute ischemic stroke: A guideline for healthcare professionals. Stroke. 2018; 49:e46-e99.
30. Seyedsaadat and Kallmes, Memantine for the treatment of ischemic stroke: experimental benefits and clinical lack of studies. Rev Neurosci. 2019; 30(2):203-220.
31. Sutherland B. A. et al. Neuroprotection for ischaemic stroke: translation from the bench to the bedside. Int J Stroke. 2012; 7(5):407-18.
32. The ATLANTIS, ECASS, and NINDS rt-PA Study Group Investigators, Tissue Plasminogen Activator for Acute Ischemic Stroke. pooled analysis of ATLANTIS, ECASS, and NINDS rt-PA stroke trials. Lancet 2004; 363: 768-774.

33. The National Institute of Neurological Disorders and Stroke rt-PA Stroke Study Group, Tissue plasminogen activator for acute ischemic stroke. N Engl J Med, 1995; 333:1581-1588.

34. Wandell P. et al., Venous thromboembolism 2011-2018 in Stockholm: a demographic study. J Thromb Thrombolysis. 2019; 48(4):668-673.

35. Wang X. C. and Shuaib A. NMDA/NR2B selective antagonists in the treatment of ischemic brain injury. Curr Drug Targets CNS Neurol Diord. 2005; 4(2):143-151

36. Won S. J. et al., Cellular and molecular pathways of ischemic neuronal death. J Biochem Mol Biol. 2002; 35(1):67-86.

What is claimed is:

1. A method of reducing neurological deficits and/or improving daily activity of living in an ischemic stroke patient receiving a recanalization therapy with a thrombolytic drug, endovascular thrombectomy (EVT), or endovascular thrombectomy with a thrombolytic drug, comprising administering to the patient a composition comprising the compound of formula (I):

[Chemical Formula 1]

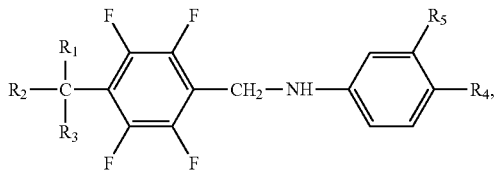

wherein
$R_1$, $R_2$, and $R_3$, are, independently, hydrogen or halogen;
$R_4$ is hydroxy, alkyl, alkoxy, halogen, alkanoyloxy, or nitro; and
$R_5$ is carboxylic acid, carboxylic acid ester, carboxyamide, sulfonic acid, halogen, or nitro, or a pharmaceutically acceptable salt thereof.

2. The method of claim 1, wherein the compound of formula (I) is selected from:
2-Hydroxy-5-(2,3,5,6-tetrafluoro-4-trifluoromethylbenzylamino)benzoic acid, (hereinafter, referred to as 2-Hydroxy-TTBA or nelonemdaz),
2-Nitro-5-(2,3,5,6-tetrafluoro-4-trifluoromethylbenzylamino)benzoic acid,
2-Chloro-5-(2,3,5,6-tetrafluoro-4-trifluoromethylbenzylamino)benzoic acid,
2-Bromo-5-(2,3,5,6-tetrafluoro-4-trifluoromethylbenzylamino)benzoic acid,
2-Methyl-5-(2,3,5,6-tetrafluoro-4-trifluoromethylbenzylamino)benzoic acid,
2-Methoxy-5-(2,3,5,6-tetrafluoro-4-trifluoromethylbenzylamino)benzoic acid,
5-(2,3,5,6-tetrafluoro-4-trifluoromethylbenzylamino)-2-trifluoromethoxybenzoic acid,
2-Nitro-4-(2,3,5,6-tetrafluoro-4-trifluoromethylbenzylamino)phenol,
2-Chloro-4-(2,3,5,6-tetrafluoro-4-trifluoromethylbenzylamino)phenol,
2-Hydroxy-5-(2,3,5,6-tetrafluoro-4-trifluoromethylbenzylamino)benzamide,
2-Hydroxy-5-(2,3,5,6-tetrafluoro-4-trifluoromethylbenzylamino)benzene sulfonic acid,
Methyl 2-hydroxy-5-(2,3,5,6-tetrafluoro-4-trifluoromethylbenzylamino)benzoate,
2-Ethanoyloxy-5-(2,3,5,6-tetrafluoro-4-trifluoromethylbenzylamino)benzoic acid,
2-Propanoyloxy-5-(2,3,5,6-tetrafluoro-4-trifluoromethylbenzylamino)benzoic acid, and
2-Cyclohexanecarbonyloxy-5-(2,3,5,6-tetrafluoro-4-trifluoromethylbenzylamino)benzoic acid,
or a pharmaceutically acceptable salt thereof.

3. The method of claim 1, wherein the compound of formula (I) is 2-hydroxy-5-(2,3,5,6-tetrafluoro-4-trifluoromethylbenzylamino)benzoic acid (nelonemdaz) or a pharmaceutically acceptable salt thereof.

4. The method of claim 1, wherein the compound of formula (I) or a pharmaceutically acceptable salt thereof is (a) in a liquid composition; or (b) lyophilized.

5. The method of claim 1, wherein the composition comprises 50 mg to 2000 mg of the compound of formula (I) or a pharmaceutically acceptable salt thereof.

6. The method of claim 1, wherein the composition comprises 50 mg to 2000 mg of the compound of formula (I) or a pharmaceutically acceptable salt thereof dissolved in water for injection at pH 8-11.

7. The method of claim 1, wherein the composition comprises tris(hydroxymethyl)aminomethane [THAM]-buffer and 50 mg to 2000 mg of the compound of formula (I) or a pharmaceutically acceptable salt thereof.

8. The method of claim 1, wherein the composition comprises a potassium salt of nelonemdaz (nelonemdazK).

9. The method of claim 1, wherein the method comprises administering to the patient a composition comprising the compound of formula (I) or a pharmaceutically acceptable salt thereof at:
(a) a dose from 250 mg to 1500 mg twice daily for 1-5 days;
(b) a total dose of 6,000 mg over 5 days;
(c) a total of 10 doses in 5 days, wherein the first dose comprises 1500 mg, and each of the remaining doses comprises 500 mg, optionally wherein each dose is administered at 12 hour-intervals;
(d) a total dose of 5,250 mg over 5 days; or
(e) a total of 10 doses in 5 days, wherein the first dose comprises 750 mg, and each of the remaining doses comprises 500 mg, optionally wherein each dose is administered at 12 hour-intervals.

10. The method of claim 1, wherein the patient is a human.

11. The method of claim 1, wherein the ischemic stroke patient receives a recanalization therapy with a thrombolytic drug.

12. The method of claim 1, wherein the ischemic stroke patient receives endovascular thrombectomy (EVT).

13. The method of claim 1, wherein the ischemic stroke patient receives endovascular thrombectomy with a thrombolytic drug.

14. The method of claim 1, wherein the thrombolytic drug is selected from recombinant tissue plasminogen activator (rt-PA), modified rt-PA, and urokinase.

15. The method of claim 14, wherein the thrombolytic drug is rt-PA.

16. The method of claim 1, wherein the endovascular thrombectomy is performed using a device selected from Trevo, Solitaire FR, and Penumbra.

17. The method of claim 1, wherein the compound of formula (I) or a pharmaceutically acceptable salt thereof is administered orally.

18. The method of claim 1, wherein the compound of formula (I) or a pharmaceutically acceptable salt thereof is administered intravenously.

19. The method of claim 1, wherein the method comprises administering to the patient a composition comprising the compound of formula (I) or a pharmaceutically acceptable salt thereof at:
   (a) a total dose of 3500 mg in 5 days;
   (b) a total of 10 doses in 5 days, wherein the first dose comprises 750 mg, and each of the remaining doses comprises 250 mg, optionally wherein each dose is administered at 12 hour-intervals;
   (c) a total dose of 3250 mg in 5 days; or
   (d) a total of 10 doses in 5 days, wherein the first dose comprises 500 mg, and each of the remaining doses comprises 250 mg, optionally wherein each dose is administered at 12 hour-interval.

* * * * *